United States Patent
Angle et al.

(10) Patent No.: US 12,161,443 B2
(45) Date of Patent: *Dec. 10, 2024

(54) SYSTEMS AND METHODS FOR DETECTING CORRUPT OR INACCURATE SENSORY REPRESENTATIONS

(71) Applicant: Paradromics, Inc., Austin, TX (US)

(72) Inventors: Matthew Angle, Austin, TX (US); Edmund Huber, San Francisco, CA (US); Richard C. Gerkin, Phoenix, AZ (US); Konrad Kording, Austin, TX (US)

(73) Assignee: Paradromics, Inc., Austin, TX (US)

( * ) Notice: Subject to any disclaimer, the term of this patent is extended or adjusted under 35 U.S.C. 154(b) by 332 days.

This patent is subject to a terminal disclaimer.

(21) Appl. No.: 17/382,232

(22) Filed: Jul. 21, 2021

(65) Prior Publication Data
US 2021/0378526 A1    Dec. 9, 2021

Related U.S. Application Data

(63) Continuation of application No. 16/351,421, filed on Mar. 12, 2019, now Pat. No. 11,071,465, which is a
(Continued)

(51) Int. Cl.
*A61B 5/00* (2006.01)
*A61B 5/01* (2006.01)
(Continued)

(52) U.S. Cl.
CPC ........ *A61B 5/02055* (2013.01); *A61B 5/0036* (2018.08); *A61B 5/01* (2013.01);
(Continued)

(58) Field of Classification Search
CPC ..... A61B 5/02055; A61B 5/01; A61B 5/7221; A61B 5/7264
See application file for complete search history.

(56) References Cited

U.S. PATENT DOCUMENTS

| | | |
|---|---|---|
| 6,171,239 B1 | 1/2001 | Humphrey |
| 6,353,754 B1 | 3/2002 | Fischell et al. |
| | (Continued) | |

FOREIGN PATENT DOCUMENTS

| | | |
|---|---|---|
| CN | 1444904 A | 10/2003 |
| CN | 1886172 A | 12/2006 |
| | (Continued) | |

OTHER PUBLICATIONS

PCT/US2017/052589 International Search Report and Written Opinion dated Nov. 27, 2017.
(Continued)

*Primary Examiner* — Eric D. Bertram
(74) *Attorney, Agent, or Firm* — Wilson Sonsini Goodrich & Rosati

(57) ABSTRACT

A system for monitoring neural activity of a living subject is provided. The system may comprise a correspondence module configured to be in communication with (1) a neural module and (2) one or more additional modules comprising a sensing module, another neural module, and/or a data storage module. The neural module(s) are configured to collect neural data indicative of perceptions experienced by the living subject. The sensing module may be configured to collect (1) sensor data indicative of real-world information about an environment around the living subject, and/or (2) sensor data indicative of a physical state or physiological state of the living subject. The data storage module may be configured to store prior neural data and/or prior sensor data. The correspondence module may be configured to measure a correspondence (a) between the neural data collected by the neural module(s) and the sensor data collected by the sensing module, (b) between the neural data collected by two or more neural modules, and/or (c) between the neural data collected by the neural module(s) and the prior data
(Continued)

stored in data storage module. The measured correspondence can be used to determine a presence, absence, or extent of a potential cognitive or physiological disturbance of the living subject.

23 Claims, 6 Drawing Sheets

Related U.S. Application Data continuation of application No. PCT/US2017/052589, filed on Sep. 20, 2017.

(60) Provisional application No. 62/397,276, filed on Sep. 20, 2016.

(51) Int. Cl.
| | |
|---|---|
| *A61B 5/0205* | (2006.01) |
| *A61B 5/11* | (2006.01) |
| *A61B 5/24* | (2021.01) |
| *A61B 5/246* | (2021.01) |
| *A61B 5/291* | (2021.01) |
| *A61B 5/377* | (2021.01) |
| *A61B 5/024* | (2006.01) |

(52) U.S. Cl.
CPC ............. *A61B 5/1112* (2013.01); *A61B 5/24* (2021.01); *A61B 5/246* (2021.01); *A61B 5/291* (2021.01); *A61B 5/377* (2021.01); *A61B 5/4824* (2013.01); *A61B 5/6802* (2013.01); *A61B 5/6847* (2013.01); *A61B 5/7221* (2013.01); *A61B 5/7264* (2013.01); *A61B 5/024* (2013.01); *A61B 5/4011* (2013.01); *A61B 5/4017* (2013.01); *A61B 2560/0242* (2013.01); *A61B 2560/0257* (2013.01); *A61B 2562/0204* (2013.01); *A61B 2562/0219* (2013.01); *A61B 2562/0223* (2013.01); *A61B 2562/0247* (2013.01); *A61B 2562/0257* (2013.01); *A61B 2562/0271* (2013.01); *A61B 2562/029* (2013.01); *A61B 2562/046* (2013.01)

(56) References Cited

U.S. PATENT DOCUMENTS

| | | | |
|---|---|---|---|
| 6,382,070 B1 | 5/2002 | Garcia et al. | |
| 6,430,443 B1* | 8/2002 | Karell | A61N 1/36036 607/57 |
| 6,834,200 B2 | 12/2004 | Moxon et al. | |
| 6,994,671 B2 | 2/2006 | Oka et al. | |
| 7,461,045 B1* | 12/2008 | Chaovalitwongse | A61B 5/369 706/52 |
| 7,970,476 B2 | 6/2011 | Chapin et al. | |
| 8,291,285 B1 | 10/2012 | Varnica et al. | |
| 8,484,081 B2 | 7/2013 | Pradeep et al. | |
| 8,547,237 B2 | 10/2013 | Adebimpe et al. | |
| 8,615,311 B2 | 12/2013 | Langhammer et al. | |
| 8,694,092 B2 | 4/2014 | Ferren et al. | |
| 8,744,563 B2* | 6/2014 | Yoshida | A61B 5/165 600/544 |
| 8,776,731 B1 | 7/2014 | Curtis et al. | |
| 8,892,208 B2 | 11/2014 | Flynn et al. | |
| 9,345,232 B2 | 5/2016 | Chapin et al. | |
| 9,358,393 B1* | 6/2016 | Lozano | A61N 1/36132 |
| 9,449,225 B2 | 9/2016 | Ginosar et al. | |
| 9,471,870 B2 | 10/2016 | Kao et al. | |
| 9,517,342 B2 | 12/2016 | Costanzo et al. | |
| 10,264,990 B2 | 4/2019 | Pasley et al. | |
| 10,327,655 B2 | 6/2019 | Angle et al. | |
| 10,537,463 B2 | 1/2020 | Kopelman | |
| 10,653,330 B2 | 5/2020 | Angle et al. | |
| 10,671,917 B1* | 6/2020 | Bhattacharyya | G06F 17/16 |
| 11,071,465 B2* | 7/2021 | Angle | A61B 5/24 |
| 2003/0105409 A1* | 6/2003 | Donoghue | A61B 5/076 600/545 |
| 2003/0158587 A1 | 8/2003 | Esteller et al. | |
| 2004/0041599 A1 | 3/2004 | Murphy | |
| 2005/0090756 A1 | 4/2005 | Wolf et al. | |
| 2005/0177058 A1* | 8/2005 | Sobell | A61B 5/16 600/545 |
| 2006/0116738 A1 | 6/2006 | Wolf et al. | |
| 2006/0165811 A1 | 7/2006 | Black et al. | |
| 2007/0095304 A1 | 5/2007 | Rosenberg et al. | |
| 2008/0082019 A1* | 4/2008 | Ludving | A61B 5/6814 600/544 |
| 2008/0226255 A1* | 9/2008 | Estes | H04N 5/782 386/223 |
| 2009/0063866 A1* | 3/2009 | Navratil | A61B 5/378 706/47 |
| 2009/0082691 A1 | 3/2009 | Denison et al. | |
| 2009/0118597 A1 | 5/2009 | Mills et al. | |
| 2009/0255801 A1* | 10/2009 | Haas | G01N 33/4836 204/600 |
| 2009/0306741 A1 | 12/2009 | Hogle et al. | |
| 2010/0081958 A1 | 4/2010 | She | |
| 2010/0100001 A1* | 4/2010 | Aguilar | A61B 5/378 600/595 |
| 2010/0286747 A1* | 11/2010 | Sabesan | A61B 5/4094 607/45 |
| 2013/0063550 A1* | 3/2013 | Ritchey | G03H 1/2294 345/207 |
| 2013/0098780 A1 | 4/2013 | Georgiou et al. | |
| 2013/0144140 A1 | 6/2013 | Frederick et al. | |
| 2013/0184558 A1* | 7/2013 | Gallant | A61B 5/0042 600/409 |
| 2013/0204152 A1* | 8/2013 | Roth | A61B 5/378 600/544 |
| 2013/0314243 A1* | 11/2013 | Le | A61B 5/316 340/870.01 |
| 2014/0018693 A1 | 1/2014 | Hou et al. | |
| 2014/0025715 A1 | 1/2014 | Yang et al. | |
| 2014/0051044 A1 | 2/2014 | Badower et al. | |
| 2014/0058528 A1* | 2/2014 | Contreras-Vidal | A61B 5/291 600/383 |
| 2014/0148657 A1 | 5/2014 | Hendler et al. | |
| 2014/0163425 A1 | 6/2014 | Tran | |
| 2014/0228701 A1 | 8/2014 | Chizeck et al. | |
| 2014/0249396 A1 | 9/2014 | Shacham-Diamand et al. | |
| 2015/0005607 A1 | 1/2015 | Cui et al. | |
| 2015/0012111 A1 | 1/2015 | Contreras-Vidal et al. | |
| 2015/0042471 A1 | 2/2015 | Park et al. | |
| 2015/0088024 A1* | 3/2015 | Sackellares | A61B 5/291 600/544 |
| 2016/0128588 A1 | 5/2016 | Melosh et al. | |
| 2016/0242690 A1 | 8/2016 | Principe et al. | |
| 2016/0279418 A1 | 9/2016 | Courtine et al. | |
| 2016/0310070 A1* | 10/2016 | Sabesan | A61B 5/318 |
| 2017/0035316 A1 | 2/2017 | Kuzniecky et al. | |
| 2017/0035317 A1* | 2/2017 | Jung | A61B 3/0025 |
| 2017/0042440 A1 | 2/2017 | Even-Chen et al. | |
| 2017/0171441 A1* | 6/2017 | Kearns | G06F 3/015 |
| 2017/0196497 A1* | 7/2017 | Ray | A61B 5/318 |
| 2017/0258390 A1* | 9/2017 | Howard | A61B 5/369 |
| 2017/0290521 A1 | 10/2017 | Angle et al. | |
| 2017/0354341 A1* | 12/2017 | Kadambi | A61B 5/369 |
| 2018/0117331 A1* | 5/2018 | Kuzniecky | A61B 5/686 |
| 2018/0365554 A1 | 12/2018 | Van Den Oord et al. | |
| 2019/0227053 A1 | 7/2019 | Rinberg et al. | |
| 2019/0333505 A1 | 10/2019 | Stavisky et al. | |
| 2020/0037942 A1* | 2/2020 | Howard | A61B 5/1124 |
| 2022/0051099 A1 | 2/2022 | Shazeer et al. | |
| 2022/0319533 A1 | 10/2022 | Van Den Oord et al. | |

FOREIGN PATENT DOCUMENTS

| | | |
|---|---|---|
| CN | 103505197 A | 1/2014 |
| CN | 103584851 A | 2/2014 |
| CN | 104605853 A | 5/2015 |
| CN | 105792745 A | 7/2016 |

(56) References Cited

FOREIGN PATENT DOCUMENTS

| | | |
|---|---|---|
| JP | 4209781 B2 | 1/2009 |
| WO | WO-2011127483 A1 | 10/2011 |
| WO | WO-2012116232 A1 | 8/2012 |
| WO | WO-2015164300 A1 | 10/2015 |
| WO | WO-2016112372 A1 | 7/2016 |
| WO | WO-2017223489 A1 | 12/2017 |
| WO | WO-2018039648 A1 | 3/2018 |
| WO | WO-2018057667 A1 | 3/2018 |

OTHER PUBLICATIONS

U.S. Appl. No. 16/351,421 Notice of Allowance dated Mar. 24, 2021.

U.S. Appl. No. 16/351,421 Office Action dated Apr. 9, 2020.

U.S. Appl. No. 16/351,421 Office Action dated Jul. 14, 2020.

Akopyan, et al. A level-crossing flash asynchronous analog-to-digital converter. 12th IEEE International Symposium on Asynchronous Circuits and Systems (ASYNC'06). IEEE, 2006. 11 pages.

Atreya, et al. Novel lossy compression algorithms with stacked autoencoders. Tech. Rep. (Dec. 11, 2009). 5 pages.

Bamford, K. Canine Olfaction: An Overview of the Anatomy. Physiology and Genetics (2015). 10 pages.

Barsakcioglu, et al. An analogue front-end model for developing neural spike sorting systems. IEEE Transactions on Biomedical Circuits and Systems 8.2 (Apr. 2014): 216-227.

Barsakcioglu, et al. Design optimisation of front-end neural interfaces for spike sorting systems. 2013 IEEE International Symposium on Circuits and Systems (ISCAS2013). IEEE, 2013. 2501-2504.

Bathellier, et al. Dynamic ensemble odor coding in the mammalian olfactory bulb: sensory information at different timescales. Neuron 57.4 (2008): 586-598.

Brody, et al. Simple networks for spike-timing-based computation, with application to olfactory processing. Neuron 37.5 (2003): 843-852.

Broome, et al. Encoding and decoding of overlapping odor sequences. Neuron 51.4 (2006): 467-482.

Caron, et al. Random convergence of olfactory inputs in the *Drosophila* mushroom body. Nature 497.7447 (2013): 113-117.

Chae, et al. A 128-channel 6 mW wireless neural recording IC with spike feature extraction and UWB transmitter. IEEE Transactions on Neural Systems and Rehabilitation Engineering 17.4 (2009): 312-321.

Chen, et al. Asynchronous biphasic pulse signal coding and its CMOS realization. 2006 IEEE International Symposium on Circuits and Systems. IEEE, 2006. 2293-2296.

Chen, et al. Compressing neural networks with the hashing trick. International Conference on Machine Learning. 2015. 10 pages.

Co-pending U.S. Appl. No. 16/058,966, inventors Angle; Matthew R et al., filed on Aug. 8, 2018.

Co-pending U.S. Appl. No. 16/276,503, inventors Angle; Matthew et al., filed on Feb. 14, 2019.

Co-pending U.S. Appl. No. 16/807,042, inventors Angle; Matthew et al., filed on Mar. 2, 2020.

Co-pending U.S. Appl. No. 18/305,318, inventors Kang; Gene et al., filed on Apr. 21, 2023.

Csicsvari et al. Massively Parallel Recording of Unit and Local Field Potentials With Silicon-Based Electrodes. J Neurophysiol 90:1314-1353 (2003).

Cury, et al. Robust odor coding via inhalation-coupled transient activity in the mammalian olfactory bulb. Neuron68.3 (2010): 570-585.

Dierikx, et al. Two-color indirect X-ray photon counting image sensor. Proc. 2013 Int. Image Sensor Workshop (IISW). 2013. 4 pages.

Dong et al. A novel bioelectronic nose based on brain-machine interface using implanted electrode recording in vivo in olfactory bulb. Biosensors and Bioelectronics 49:263-269 (Nov. 15, 2013).

EP17844547.4 Extended European Search Report dated Mar. 12, 2020.

Fleischmann et al. Mice with a "Monoclonal Nose": Perturbations in an Olfactory Map Impair Odor Discrimination. Neuron 60(6):1068-1081 (Dec. 26, 2008).

Friedrich, et al. Dynamic optimization of odor representations by slow temporal patterning of mitral cell activity. Science291.5505 (2001): 889-894.

Goodfellow, et al. Measuring invariances in deep networks. Advances in Neural Information Processing Systems. 2009. 9 pages.

Harris, et al. Pulse-based signal compression for implanted neural recording systems. 2008 IEEE International Symposium on Circuits and Systems. IEEE, 2008. 344-347.

Hopfield, J. Pattern recognition computation using action potential timing for stimulus representation. Nature 376.6535 (1995): 33-36.

Johnson, et al. Chemotopic odorant coding in a mammalian olfactory system. Journal of Comparative Neurology 503.1 (2007): 1-34.

Junek, et al. Olfactory coding with patterns of response latencies. Neuron 67.5 (2010): 872-884.

Kamboh, et al. Computationally efficient neural feature extraction for spike sorting in implantable high-density recording systems. IEEE Transactions on Neural Systems and Rehabilitation Engineering 21.1 (2013): 1-9.

Kamboh, et al. On-chip feature extraction for spike sorting in high density implantable neural recording systems. 2010 Biomedical Circuits and Systems Conference (BioCAS). IEEE, 2010.13-16.

Koulakov, et al. Olfactory coding with all-or-nothing glomeruli. Journal of neurophysiology 98.6 (2007): 3134-3142.

Kozmin, et al. Level-crossing ADC performance evaluation toward ultrasound application. IEEE Transactions on Circuits and Systems I: Regular Papers 56.8 (2009): 1708-1719.

Kwon, et al., NeuroQuest: A comprehensive analysis tool for extracellular neural ensemble recordings, J Neurosci Methods. Feb. 15, 2012; 204(1): 189-201. doi:10.1016/j.jneumeth.2011.10.027.

Laurent, et al. Encoding of olfactory information with oscillating neural assemblies. Science 265.5180 (1994): 1872-1875.

Lee, et al. Convolutional deep belief networks for scalable unsupervised learning of hierarchical representations. Proceedings of the 26th annual international conference on machine learning. ACM, 2009. 8 pages.

MacLeod, et al. Who reads temporal information contained across synchronized and oscillatory spike trains?. Nature 395.6703 (1998): 693-698.

Margrie, et al. Theta oscillation coupled spike latencies yield computational vigour in a mammalian sensory system. The Journal of physiology 546.2 (2003): 363-374.

Marshall et al. Detection of Volatile Indicators of Illicit Substances by the Olfactory Receptors of *Drosophila melanogaster*. Chemical Senses 35(7):613-625 (Sep. 2010). Advance Access publication Jun. 7, 2010. DOI: https://doi.org/10.1093/chemse/bjq050 .

Martins et al. A CMOS IC for Portable EEG Acquisition Systems. IEEE Transactions on Instrumentation and Measurement 47(5):1191-1196 (Oct. 1998).

Morimoto, et al. Classifying the brain's motor activity via deep learning. Stanford University, CS 229 Machine Learning (2014). 5 pages.

Navajas, et al. Minimum requirements for accurate and efficient real-time on-chip spike sorting. Journal of Neuroscience Methods 230 (2014): 51-64.

Nurse, et al. A generalizable brain-computer interface (BCI) using machine learning for feature discovery. PloS One 10.6 (2015): e0131328. 22 pages.

Nurse, et al. Decoding EEG and LFP signals using deep learning: heading TrueNorth. Proceedings of the ACM International Conference on Computing Frontiers. ACM, 2016. 259-266.

Paraskevopoulou, et al. Feature extraction using first and second derivative extrema (FSDE) for real-time and hardware-efficient spike sorting. Journal of Neuroscience Methods 215.1 (2013): 29-37.

Paraskevopoulou, et al. Hierarchical Adaptive Means (HAM) clustering for hardware-efficient, unsupervised and real-time spike sorting. Journal of Neuroscience Methods 235 (2014): 145-156.

(56) References Cited

OTHER PUBLICATIONS

PCT/US2017/048759 International Search Report and Written Opinion dated Nov. 8, 2017.
Ranzato, et al. Unsupervised learning of invariant feature hierarchies with applications to object recognition. Proc. Computer Vision and Pattern Recognition Conference (CVPR'07). IEEE Press. vol. 127. 2007. 9 pages.
Rapoport et al. A Biomimetic Adaptive Algorithm and Low-Power Architecture for Implantable Neural Decoders. Proceedings of the 31st Annual International Conference of the IEEE Engineering in Medicine and Biology Society: Engineering the Future of Biomedicine, EMBC 2009, IEEE, pp. 4214-4217 (Sep. 3, 2009).
Rastogi, et al. Integrate and fire circuit as an ADC replacement. 2011 IEEE International Symposium of Circuits and Systems (ISCAS). IEEE, 2011. 2421-2424.
Rogers, C. Ultra-Low power analog circuits for spike feature extraction and detection from extracellular neural recordings. Diss. University of Florida, 2007. 131 pages.
Rogers, et al. A pulse-based feature extractor for spike sorting neural signals. 2007 3rd International IEEE/EMBS Conference on Neural Engineering. IEEE, 2007. 490-493.
Saeed, et al. Hardware architecture for on-chip unsupervised online neural spike sorting. 2013 6th International IEEE/EMBS Conference on Neural Engineering (NER). IEEE, 2013. 1319-1322.
Schaefer, et al. Psychophysical properties of odor processing can be quantitatively described by relative action potential latency patterns in mitral and tufted cells. Frontiers in systems neuroscience 6 (2012): 30. 8 pages.
Schmidhuber, J. Deep learning in neural networks: An overview. Neural Networks 61 (Oct. 8, 2014): 85-117.
Scribner, D. et al., A retinal prosthesis technology based on CMOS microelectronics and microwire glass electrodes. IEEE transactions on biomedical circuits and systems, 1(1); Mar. 2007: p. 73-84.
Shusterman, et al. Precise olfactory responses tile the sniff cycle. Nature neuroscience 14.8 (2011): 1039-1044.
Stober, et al. Deep feature learning for EEG recordings. arXiv preprint arXiv:1511.04306 (2015). 24 pages.
Stober, et al. Using Convolutional Neural Networks to Recognize Rhythm▨ Stimuli from Electroencephalography Recordings. Advances in Neural Information Processing Systems. 2014. 9 pages.
Todorova, et al. To sort or not to sort: the impact of spike-sorting on neural decoding performance. Journal of Neural Engineering 11.5 (Epub Aug. 1, 2014): 056005. 13 Pages.
U.S. Appl. No. 16/275,205 Office Action dated Sep. 27, 2019.
U.S. Appl. No. 16/058,966 Office Action dated Oct. 29, 2020.
U.S. Appl. No. 16/275,205 Notice of Allowance dated Apr. 8, 2020.
U.S. Appl. No. 16/275,205 Notice of Allowance dated Dec. 12, 2019.
U.S. Appl. No. 17/382,232 Office Action dated Jun. 5, 2023.
Vizcay et al. Odorant recognition using biological responses recorded in olfactory bulb of rats. Computers in Biology and Medicine 56:192-199 (Jan. 1, 2015).
Wehr, et al. Odour encoding by temporal sequences of firing in oscillating neural assemblies. Nature 384.6605 (1996): 162-166.
Wilson, et al. Concentration invariant odor coding. bioRxiv (2017): 125039. 27 pages.
Xu, J. Event-based compression circuits for neural recording. Diss. University of Florida, 2011. 153 pages.
Yen, et al. An integrated recording system using an asynchronous pulse representation. 2009 4th International IEEE/EMBS Conference on Neural Engineering. IEEE, 2009. 392-402.
Zheng, et al. An adaptive 16/64 kHz, 9-bit SAR ADC with peak-aligned sampling for neural spike recording. 2014 IEEE International Symposium on Circuits and Systems (ISCAS). IEEE, 2014. 2385-2388.

\* cited by examiner

SYSTEMS AND METHODS FOR DETECTING CORRUPT OR INACCURATE SENSORY REPRESENTATIONS

CROSS-REFERENCE TO RELATED APPLICATION

This application is a continuation application of U.S. application Ser. No. 16/351,421, filed Mar. 12, 2019, now issued as U.S. Pat. No. 11,071,465, which is a continuation application of International Patent Application No. PCT/US2017/052589, filed on Sep. 20, 2017, which application claims priority to U.S. Provisional Patent Application No. 62/397,276, filed on Sep. 20, 2016, which applications are incorporated herein by reference in their entirety.

BACKGROUND

Disorders of the nervous system, such as traumatic brain or nerve injury or neuropsychiatric illness can result in a dramatic misalignment between a person's perception of their surroundings and the true state of their physical environment. Such a misalignment may be indicative of corrupt or inaccurate sensory perceptions. This is particularly true in the case of sensory hallucinations. Patients suffering from mental disorders such as schizophrenia may experience a sensory stimulus that does not coincide with the patients' real-world environment. For example, a patient may experience an auditory perception (appear to hear sounds such as voices), when in fact no such sounds are being emanated in the surroundings. In some cases, the patient may be aware that the sensory stimulus is not real, and is able to revert back to reality. However, in other cases, the patient may be unable to distinguish hallucinated perceptions from reality. In still other cases, the patient may have partial awareness that the sensory stimulus is not real, and may be able to partially revert back to reality.

Thus, there is a need for systems and methods that can detect inaccuracies or distortions in neural representations of sensory stimuli, with respect to real-world environmental stimuli. Such inaccuracies or distortions may indicate that the neural representations are corrupted, and that a patient may be experiencing hallucinations or other corrupt or inaccurate sensory perceptions. There is a need to intervene when these events occur, potential alerting the patient, a provider, a caretaker, or a monitoring system. There is also a further need for systems and methods that can correct for these inaccurate neural representations, by reducing or eliminating the corrupt or inaccurate perceptions.

SUMMARY

The system and methods described herein can address at least the above needs. Embodiments of the system may be particularly well suited for use in brain research applications, as well as in clinical applications, such as in the development of methods for treating nervous system disorders.

According to one aspect of the invention, a system for monitoring neural activity is provided. The system may comprise: a neural data analysis module configured to extract neural data from a plurality of neural signals that are collected using one or more neural interface probes implanted into a living subject; a sensing module configured to collect sensor data indicative of real-world environmental stimuli in a vicinity of the living subject; and a correspondence module in communication with the neural data analysis module and the sensing module, wherein the correspondence module is configured to generate an output based on the neural data and the sensor data, wherein the output is indicative of an agreement or disagreement between external sensors and neural data between the real-world environmental stimuli and neural perceptions experienced by the living subject.

In some embodiments, the neural data analysis module may be configured to extract neural data from a plurality of signals that are collected from the nervous system of a living subject using one or more devices. The sensing module may be configured to collect sensor data indicative of real-world signals from an environment around or within the living subject. The correspondence module may be in communication with the neural data analysis module and the sensing module, and configured to generate an output based on the neural data and the sensor data, wherein the output is indicative of a correspondence between the environment and neural perceptions experienced by the living subject.

In some embodiments, the correspondence module may be configured to detect corrupt or inaccurate sensory representations from the correspondence based on statistical models, information theory, or machine learning algorithms.

In some embodiments, the plurality of signals collected from the nervous system may comprise electrical signals, magnetic signals, and/or optical signals. The aforementioned one or more devices may comprise a neural interface probe provided in a massively parallel configuration. For example, the neural interface probe may comprise a microwire bundle bonded onto a CMOS sensing array. In other embodiments, the neural interface probe may comprise an array of silicon microelectrode probes that are bonded onto a CMOS sensing array such that each electrode site is routed to a unique array position. In some cases, the one or more devices may comprise an electroencephalography (EEG) device. In other embodiments, there may be as few as one sensor detecting activity in the nervous system.

In some embodiments, the neural data may be represented as one or more analog or digital signals representing activity recorded in the nervous system. In some cases, the neural data may be stored from previously recorded activity in the nervous system of the living subject or other living subjects.

In some embodiments, the sensing module may comprise a plurality of sensors selected from the group consisting of vision sensors, audio sensors, touch sensors, location sensors, inertial sensors, proximity sensors, heart rate monitors, temperature sensors, altitude sensors, attitude sensors, pressure sensors, humidity sensors, vibration sensors, chemical sensors, and electromagnetic field sensors. One or more sensors of the sensing module may also record data from a region of the nervous system. For instance, the sensors of the sensing module may record data from a different region of the brain than the region from which the neural interface probe records. In some cases, the sensors may record data from the same region of the brain from which the neural interface probe records. One or more of the plurality of sensors in the sensing module may be provided in a mobile device, or in a wearable device configured to be worn by the living subject.

In some embodiments, the one or more neural interface probes may be implanted in different areas of the brain of the living subject that are associated with different sensory processing. The different sensory processing may include visual, auditory, tactile, taste, smell, position/movement, and/or interoception processing. One or more sensors may be configured to collect real-world environmental stimuli related to each of the different sensory processing. In one instance, at least one neural interface probe may be implanted in an area of the living subject's brain associated with auditory processing, and wherein the sensing module may comprise at least one microphone configured to collect audio data in the vicinity of the living subject. In another instance, at least one neural interface probe may be implanted in an area of the living subject's brain associated with visual processing, and wherein the sensing module may comprise at least one camera configured to collect image data of the living subject's surrounding. In yet another instance, at least one neural interface probe may be implanted in an area of the living subject's brain associated with spatial or location awareness, and wherein the sensing module may comprise at least one global positioning sensor (GPS) sensor configured to collect positional data of the living subject.

The correspondence module can be configured to determine correspondence between the neural data and the sensor data. Additionally or optionally, the correspondence module can be configured to determine correspondence between different sets of neural data. In some embodiments, the correspondence module can be implemented via a statistical model. In some cases, the correspondence module can be configured to perform information theoretic calculations. The correspondence module can be implemented via machine learning algorithms.

In some embodiments, the correspondence module may be configured to analyze the neural data and the sensor data using a statistical model, information theory, or machine learning. The statistical model may be based on either frequentist or Bayesian statistics. In some instances, the information theoretic approach may be based on mutual information or related quantities. In some instances, the statistical model may be implemented in a neural network or any other approach to machine learning. The calculations in the correspondence module may be calculated using data from two or more modules of the same type, or modules of different types. The inputs and outputs of this module may be univariate or multivariate.

In some embodiments, the correspondence module may further comprise a decoder configured to reconstruct neural representations of sensory perceptions from the neural data. In one instance, the decoder may comprise a speech recognition software configured to reconstruct neural representations of speech and sounds, and wherein said neural representations may be recorded within the neural signals collected by one or more neural interface probes that are implanted in an area of the living subject's brain associated with auditory processing. The correspondence module may be configured to compare the reconstructed neural representations of speech and sounds to actual audio data recorded by the sensing module in the living subject's vicinity, so as to determine (1) whether the reconstructed neural representations of speech and sounds correspond to real-life audio stimuli, or (2) whether the reconstructed neural representations of speech and sounds correspond to auditory hallucinations. In another instance, the decoder may comprise an image recognition software configured to reconstruct neural representations of visual data, and wherein said neural representations may be recorded within the neural signals collected by one or more neural interface probes that are implanted in an area of the living subject's brain associated with visual processing. The correspondence module may be configured to compare the reconstructed neural representations of visual data to actual image data recorded by the sensing module in the living subject's vicinity, so as to determine (1) whether the reconstructed neural representations of visual data correspond to real-life visual stimuli, or (2) whether the reconstructed neural representations of visual data correspond to visual hallucinations.

The correspondence module can be configured to generate an error signal based on the degree of correspondence between neural data and sensor data. Additionally or optionally, the correspondence module can configured to generate an error signal based on different sets of neural data. A high error signal may result from low correspondence, and may be indicative that the living subject is experiencing inaccurate neural perceptions. The high error signal may indicate that patterns of neural activity are atypical and/or unhealthy patterns of neural activity. Conversely, a low error signal may result from high correspondence, and may indicate that the living subject is experiencing neural perceptions matching the real-world environmental stimuli. The low error signal may indicate that patterns of neural activity are typical and/or healthy patterns of neural activity. In some cases, the high error signal may be indicative of the living subject experiencing a hallucination episode.

In some embodiments, the correspondence module may further drive an error detector configured to generate an error signal related to the lack of correspondence. The error signal may be indicative that the living subject is experiencing inaccurate neural perceptions when the perception error exceeds the predetermined correspondence threshold. A low error signal may indicate that the living subject is experiencing neural perceptions matching the real-world environmental stimuli, whereas a high error signal may be indicative of the living subject experiencing an episode of inaccurate sensory perception. In some cases, the error signal may comprise one or more visual signals, audio signals, or vibration signals that are used to alert the living subject or a healthcare provider entity. The system may be in communication with a remote server associated with a healthcare provider entity.

The error signal may be derived from a technique such as canonical correlation analysis (CCA) or any other linear or non-linear analogue that finds the correspondence between lower-dimensional representations of the sensor data and the neural data. The mapping from such a technique can generate a correspondence, and a lack of correspondence can drive the error signal.

The error signal may be vector-valued. It may simultaneously contain distinct values corresponding to individual measures of correspondence in different combinations of sensors and neural data streams. It may also contain values corresponding to analysis of previous measurements or values produced by any computation.

The error signal may in some instances be driven not by lack of correspondence between neural and sensor data, but simply by neural data which is determined to be unlikely in a healthy mental state. For example, the neural data might exhibit patterns characteristic of a hallucination, based on previous episodes of health or hallucination in the same or other subjects, even if the sensor data is insufficient or unnecessary for determining this.

The error signal may be processed by a decision module, which may use the strength of the evidence of hallucination represented by the error signal to generate a decision about system action. The decision module may be based on a simple error signal threshold. Alternatively, the decision module may be based on Bayesian inference about the error signal in combination with a prior model of the distribution of that signal under various scenarios. Alternatively, the decision module may be based on machine learning techniques related to classification.

The decision module may comprise different algorithms and/or thresholds for different specific decisions. For example, the decision about whether to alert the user may require a certain error signal magnitude, whereas the decision about whether to administer medication may require another error signal magnitude.

In some embodiments, the system may further comprise a neural stimulator configured to receive the output from the decision module, and generate neural stimuli depending indirectly on the strength of the error signal. The neural stimulator may be configured to receive an action signal from the decision module, and generate neural stimuli depending on the action signal. The action signal may be related to the correspondence between the neural data and the sensor data. The neural stimulator may be configured to generate the neural stimuli when the action signal indicates that the correspondence between the neural data and the sensor data is low. In some instances, the neural stimulator may be an implanted medical device configured to automatically dispense a predetermined dosage of medication to the living subject when the action signal indicates that the correspondence between the neural data and the sensor data is low. The neural stimulator may also be an implanted medical device configured to automatically vary a dispensed dosage of medication to the living subject depending on the degree of correspondence. The medication may be designed to alter a mental state of the living subject to improve the expected correspondence between the neural data and the sensor data, or to rectify the expected neural data. In some embodiments, the neural stimulator may be provided on one or more neural interface probes, and configured to deliver electrical pulses to the living subject when the correspondence is low. The electrical pulses can be designed to alter a mental state of the living subject to improve the correspondence.

In some embodiments, the neural stimulator may thus generate the neural stimuli when the correspondence is below a threshold, or when it exhibits some other properties that trigger the decision module to issue a neural stimulation directive. In one instance, the neural stimulator may be an implanted medical device configured to automatically dispense a predetermined dosage of medication to the living subject when the decision module makes such an indication. Alternatively, the neural stimulator may be an implanted medical device configured to automatically vary a dispensed dosage of medication to the living subject in such a situation. The medication may be designed to alter a mental state of the living subject to improve correspondence. In some cases, the neural stimulator may be provided on the one or more neural interface probes, and configured to deliver electrical pulses to the living subject. The electrical signals may be designed to alter a mental state of the living subject to improve the degree of correspondence.

In some embodiments, the system may exhibit negative feedback such that the output of the decision module results in actions that improve correspondence, reducing the error signal, and causing the decision module to cease the action. For instance, upon detection of an episode of inaccurate sensory processing, the decision module may administer a medication that reduces or eliminates the episode. This may reduce the error signal, resulting in a decrease in the dosage of the medication administered.

In some embodiments, the correspondence module may be configured to receive and process (1) the neural data from the neural data analysis module and (2) the sensor data from the sensing module, substantially in real-time.

In some embodiments, the correspondence module may receive sensor data or neural data that was previously recorded. This may occur via on-board storage of that data, or by sending it from another module. In some instances, previously recorded sensor data or neural data may also be used to compute correspondence, in conjunction with data recorded substantially in real-time. This previously recorded data may be used to establish a baseline or prior distribution of data for a sensory or neural modality.

In some embodiments, the correspondence module may contain labeled data that algorithms can use to make a determination about correspondence. For example it may contain many examples of neural data patterns, some of which are labeled as "normal" and others of which are labeled as "atypical". For example, a machine learning classifier could use these labels to assist in making a classification of newly recorded data.

In some embodiments, labeled data may be added to the module after the device is implanted or attached, via wired or wireless means, or via processing of signals that it directly records from the nervous system.

In some embodiments, the correspondence module may be modified according to the contents of the labeled data that it can access at any given time. For example, a classifier may be trained on this labeled data to improve a determination of correspondence based on new data.

In some embodiments, labels may be provided to data based on external actions by authorized users. For example, the patient him/herself or a clinician might examine the data in real time or offline and label the data as being associated with a normal state or with a hallucination, based on their subjective assessment or any other analysis.

According to another aspect of the invention, a system for monitoring neural activity of a living subject is provided. The system may comprise a correspondence module configured to be in communication with (1) a neural module and (2) one or more additional modules comprising a sensing module, another neural module, and/or a data storage module. The neural module(s) may be configured to collect neural data indicative of perceptions experienced by the living subject. The sensing module may be configured to collect (1) sensor data indicative of real-world information about an environment around the living subject, and/or (2) sensor data indicative of a physical state or physiological state of the living subject. The data storage module may be configured to store prior neural data and/or prior sensor data. The correspondence module may be configured to measure a correspondence (a) between the neural data collected by the neural module(s) and the sensor data collected by the sensing module, (b) between the neural data collected by two or more neural modules, and/or (c) between the neural data collected by the neural module(s) and the prior data stored in data storage module. The measured correspondence can be used to determine a presence, absence, or extent of a potential cognitive or physiological disturbance of the living subject.

In some embodiments, the measured correspondence may comprise a level of agreement or disagreement (a) between the neural data collected by the neural module(s) and the sensor data collected by the sensing module, (b) between the neural data collected by two or more neural modules, and/or (c) between the neural data collected by the neural module(s) and the prior data stored in data storage module. The level of agreement or disagreement may be measured along a continuum. The level of agreement or disagreement may comprise a multivariate vector. The correspondence module may be configured to measure the correspondence using statistical models, information theory, or machine learning algorithms. The correspondence module may be configured to measure the correspondence (b) between the neural data collected by the two or more neural modules, without requiring or utilizing some or all of the sensor data collected by the sensing module. The correspondence module may be configured to measure the correspondence (c) between the neural data collected by the neural module(s) and the prior data stored in data storage module, without requiring or utilizing some or all of the sensor data collected by the sensing module.

In some embodiments, the system may further comprise a decision module configured to determine the presence, absence, or extent of the potential cognitive or physiological disturbance based on the measured correspondence. The decision module may be further configured to generate one or more alerts to the living subject and/or a healthcare provider. The alerts may be indicative of the presence, absence, or extent of the potential cognitive or physiological disturbance. In some embodiments, the decision module may be further configured to generate one or more control signals to one or more therapeutic delivery devices, to deliver electrical stimulation and/or pharmaceutical intervention to mitigate the potential cognitive or physiological disturbance.

A method for monitoring neural activity of a living subject is provided in accordance with a further aspect of the invention. The method may comprise: providing a correspondence module configured to be in communication with (1) a neural module and (2) one or more additional modules comprising a sensing module, another neural module, and/or a data storage module. The neural module(s) may be configured to collect neural data indicative of perceptions experienced by the living subject. The sensing module may be configured to collect (1) sensor data indicative of real-world information about an environment around the living subject, and/or (2) sensor data indicative of a physical state or physiological state of the living subject. The data storage module may be configured to store prior neural data and/or prior sensor data. The method may further comprise measuring, with aid of the correspondence module, a correspondence (a) between the neural data collected by the neural module(s) and the sensor data collected by the sensing module, (b) between the neural data collected by two or more neural modules, and/or (c) between the neural data collected by the neural module(s) and the prior data stored in data storage module. The measured correspondence can be used to determine a presence, absence, or extent of a potential cognitive or physiological disturbance of the living subject.

A method for monitoring neural activity is provided in accordance with another aspect of the invention. The method may comprise: obtaining neural data from a neural data analysis module, wherein the neural data is extracted from a plurality of neural signals collected using one or more neural interface probes implanted into a living subject; obtaining sensor data from a sensing module, wherein the sensor data is indicative of real-world environmental stimuli in a vicinity of the living subject; and generating, via a correspondence module in communication with the neural data analysis module and the sensing module, an output based on the neural data and the sensor data, wherein the output is indicative of correspondence between the real-world environmental stimuli and neural perceptions experienced by the living subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Embodiments of the disclosure described herein can enable real-time detection and correction of inaccurate neural perception applicable to certain healthcare areas. For example, the methods and systems disclosed herein can be used to monitor the mental states of patients suffering from certain mental disorders, and/or improve their state by correcting for such inaccurate neural perception errors. The data that is collected can be used to help healthcare providers and users effectively manage those mental disorders. In some cases, the data may be used by healthcare organizations or insurance companies to tailor preventive behavioral health programs for users, which can help users to improve their health and well-being.

The methods and systems described herein can be configured to record neural activity, and detect corrupt or inaccurate sensory representations from the neural activity based on information about the real-world environment. The real-world environmental information can be obtained through the use of one or more sensors mounted on a patient's body, backpack, clothing, etc., or implanted.

The methods and systems described herein utilize developments in two different fields: neurotechnology and statistical computation. It is increasingly possible to measure activity in the nervous system with impressive accuracy. For instance, with the advent of new high-density microelectrode recording techniques, neural activity can now be sampled using hundreds of thousands of independent channels. Accordingly, sufficient information relating to ongoing neural activity can be collected, and used to determine if this activity is consistent with expected sensory representations. Machine learning techniques have dramatically advanced the fields of computer vision and advanced audio processing (especially image recognition and speech recognition). By leveraging the above developments, the methods and systems described herein can extract high-level representations of audio-visual information, that can be used as reference for checking whether the reconstructed brain signals accurately correspond with actual real-world environmental stimuli.

Next, various embodiments of the disclosure will be described with reference to the drawings.

Figure 1:
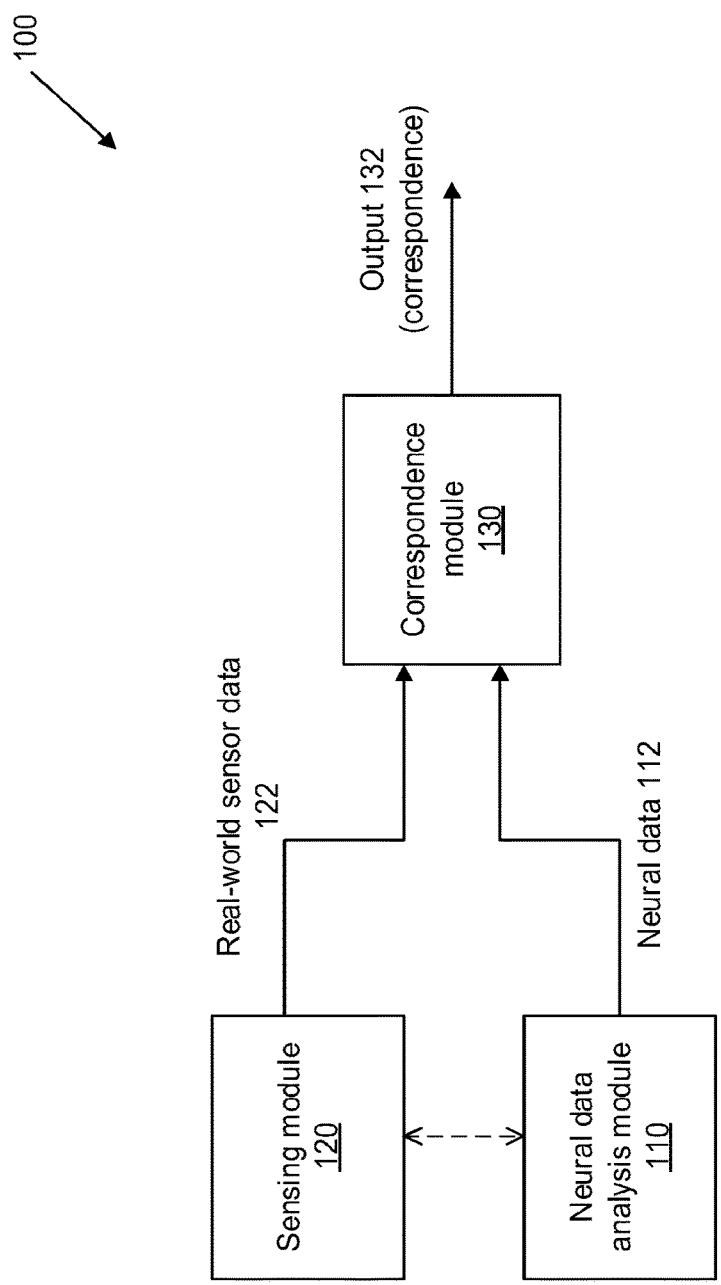
FIG. 1 illustrates a neural data correspondence system, in accordance with some embodiments.

FIG. 1 illustrates a neural data correspondence system, in accordance with some embodiments. In one aspect, a neural data correspondence system 100 may include a neural data analysis module 110, a sensing module 120, and a correspondence module 130. Each of the modules 110, 120, and 130 may be operatively connected to one another via a network or any type of communication link that allows the transmission of data from one component to another.

As previously described, a patient suffering from mental disorders may experience corrupt or inaccurate sensory perceptions. For instance, the patient may suffer from an auditory or visual hallucination, which is a perception in the absence of external stimuli that has qualities of real perception. Corrupt or inaccurate sensory perceptions can also be associated with drug use, sleep deprivation, psychosis, and delirium tremens. Corrupt or inaccurate sensory perceptions can occur in any sensory modality—visual, auditory, olfactory, gustatory, tactile, proprioceptive, equilibrioceptive, nociceptive, thermoceptive, chemoreceptive, and chronoceptive. To a patient, corrupt or inaccurate sensory perceptions can be vivid, substantial, and perceived to be located in external objective space. For example, auditory and visual hallucinations are common in patients suffering from schizophrenia. In other cases, the corrupt or inaccurate sensory perceptions may be characterized by brain activity becoming out of sync with the surroundings in a meaningful manner. For instance, patients with Alzheimer's disease or other forms of dementia may be characterized by a perception of being at home when a patient is actually in a hospital, or of no longer recognizing a person who should be extremely familiar to the patient. The correspondence system of FIG. 1 can be used to determine whether a patient is experiencing corrupt or inaccurate sensory perceptions or the onset of corrupt or inaccurate sensory perceptions, using real-world sensor data collected via one or more sensors mounted on the patient's body.

The neural data analysis module 110 may be configured to receive neural signals. The neural signals may be collected using wires, microelectrodes, optical sensors, magnetic field sensors, or any other sensors that can record the activity the nervous system, or which the brain is one part. The plurality of wires or microelectrodes may be part of one or more massively parallel neural interface probes that are configured to be implanted into one or more areas of a person's brain. The one or more neural interface probes can be configured to record information associated with neural activity and produce an output that represents neural activity. In some embodiments, the neural data analysis module may generate a signal representative of a pattern of neural activity. The neural code may comprise representations of one or more neural activities associated with a plurality of neural events detected from the neural signals.

In some cases, the neural interface probes may comprise one or more neural detection channels. For instance, the neural interface probes may comprise more than 10, more than 100, more than 1000, more than 10000, more than 100000, or more than 1000000 neural detection channels. The neural detection channels may comprise electrodes, microwires, optical sensors, magnetic field sensors, or any other sensor. In some embodiments, the one or more neural interface probes may include a microwire bundle bonded to a CMOS array. In other embodiments, the one or more neural interface probes may include an array of silicon microelectrode probes that are bonded to a CMOS array, such that each electrode site is routed to a unique array position. In other embodiments, the neural interface may consist of scalp electrodes. In other embodiments, the neural interface may consist of electrodes placed on the surface of the brain or the surface of the dura mater. In other embodiments, the neural interface may record magnetic or optical signals from the nervous system.

The massively parallel neural interface probes can be implanted into different areas of the brain associated with different sensory processing (e.g., visual, auditory, tactile, taste, smell, position/movement, interoception, etc.). In one example, one or more neural interface probes may be implanted in an area of the brain associated with auditory processing, such as the auditory cortex. In another example, one or more neural interface probes may be implanted in an area of the brain associated with visual processing, such as the primary visual cortex or fusiform gyms.

In yet another example, one or more neural interface probes may be implanted in an area of the brain associated with spatial or locational awareness. For instance, the one or more neural interface probes may be implanted in the hippocampus and configured to record neural signals from "place" cells located in the hippocampus. Alternatively, the one or more neural interface probes may be implanted in the entorhinal cortex and configured to record neural signals from "grid" cells located in the entorhinal cortex.

The sensing module 120 may include one or more types of sensors that are configured to detect signals that mostly emanate from outside the patient. These signals are indicative of reality, as opposed to the corrupt or inaccurate sensory perceptions that a patient may be experiencing. The signals may come from many different modalities, including visual, auditory, tactile, taste, smell, position/movement, and/or interoception.

Examples of types of sensors may include inertial sensors (e.g. accelerometers, gyroscopes, and/or gravity detection sensors, which may form inertial measurement units (IMUs)), location sensors (e.g. global positioning system (GPS) sensors, mobile device transmitters enabling location triangulation), heart rate monitors, external temperature sensors, skin temperature sensors, capacitive touch sensors, sensors configured to detect a galvanic skin response (GSR), vision sensors (e.g. imaging devices capable of detecting visible, infrared, or ultraviolet light, such as cameras), proximity or range sensors (e.g. ultrasonic sensors, lidar, time-of-flight or depth cameras), altitude sensors, attitude sensors (e.g. compasses), pressure sensors (e.g. barometers), humidity sensors, vibration sensors, audio sensors (e.g. microphones), and/or field sensors (e.g. magnetometers, electromagnetic sensors, radio sensors).

The sensing module may further include one or more devices capable of emitting a signal into an environment. For instance, the sensing module may include an emitter along an electromagnetic spectrum (e.g. visible light emitter, ultraviolet emitter, infrared emitter). The sensing module may include a laser or any other type of electromagnetic emitter. The sensing module may emit one or more vibrations, such as ultrasonic signals. The sensing module may emit audible sounds (e.g. from a speaker). The sensing module may emit wireless signals, such as radio signals or other types of signals.

In some cases, one or more of the sensors may establish an absolute, relative, or contextual location. For instance, one or more of the sensors may be a global positioning system (GPS) sensor that determines the person's longitude and latitude. Such a GPS sensor may provide absolute location, such as that the person is located at 39.7392° N, 104.9903° W. The one or more sensors may be any sensor that determines an absolute location. As another example, one or more of the sensors may be a wireless detector that receives a signal from a specific location. Such a detector may provide relative location, such as that the person is located 300 meters north of their house. The one or more sensors may be any sensor that determines a relative location. As yet another example, one or more of the sensors may be a sensor that provides contextual information, such as that the person is at their place of work. The one or more sensors may be any sensor that determines a contextual location.

In some embodiments, the sensing module may be configured to perform sensor fusion on different types of sensor data. For example, the sensor module may include a sensor/receiver for GPS, an inertial measurement unit (IMU), another sensor for cell tower distances, etc. These sensors can be used to obtain different estimates of a location. The sensor fusion may include the use of an algorithm and a Kalman filter to combine estimators, that have weakly correlated errors, into a combined estimator whose error is less than the error of any one of the original estimators. Accordingly, the different sensors can be used to compensate for deficiencies/inaccuracies of the other. Alternatively, the data from the sensors may be combined and its dimensionality reduced by canonical correlation analysis or an analogous technique (e.g. deep canonical correlation analysis or deep general canonical correlation analysis) focused on finding the correspondence between the multivariate sensor data and the multivariate neural data.

In some embodiments, one or more sensors of the sensing module may be incorporated into a wearable device. Examples of wearable devices may include smartwatches, wristbands, glasses, gloves, headgear (such as hats, helmets, virtual reality headsets, augmented reality headsets, head-mounted devices (HMD), headbands), pendants, armbands, leg bands, shoes, vests, motion sensing devices, etc. The wearable device may be configured to be worn on a part of a user's body (e.g. a smartwatch or wristband may be worn on the user's wrist).

The correspondence module can be used to detect corrupt or inaccurate sensory representations. The correspondence module may be configured to receive (a) neural data 112 from the neural data analysis module 110 and (b) real-world sensor data 122 from the sensing module 120. The correspondence module may further analyze and compare the neural data 112 and sensor data 122, so as to generate an output 132 that is indicative of a degree of correspondence between perceptions obtained from the neural data with respect to the real-world environmental stimuli. The degree of correspondence may indicate whether a patient is experiencing corrupt or inaccurate sensory perceptions or is accurately experiencing reality. In some cases, the degree of correspondence may indicate an extent or severity of a patient's corrupt or inaccurate sensory perceptions.

The correspondence module may be implemented anywhere within the neural data correspondence system and/or outside of the neural data correspondence system. In some embodiments, the correspondence module may be implemented on a server. In other embodiments, the correspondence module may be implemented on a wearable device described elsewhere herein. In still other embodiments, the correspondence module may be implemented on a portable electronic device, such as a smartphone, tablet computer, or laptop computer. Additionally, the correspondence module may be implemented in the neural data analysis module. Alternatively, the correspondence module may be implemented in the sensor module. In other embodiments, the correspondence module may be implemented in both the neural data analysis module and the sensor module, or external to both the neural data analysis module and the sensor module. The correspondence module may be implemented using software, hardware, or a combination of software and hardware in one or more of the above-mentioned components within the neural data correspondence system.

The correspondence module may be capable of determining a correspondence between the neural data 112 and the real-world sensor data 122 using algorithms based in part on statistical analysis, information theory, machine learning, signal processing, pattern recognition, and/or detection theory. The correspondence module may utilize a supervised machine learning method, a semi-supervised machine learning method, or a supervised machine learning method known to one having skill in the art. An algorithm may assume a certain statistical model and try to detect whether a patient is experiencing corrupt or inaccurate sensory perceptions based on the model. The algorithm may also estimate a different statistical model for each patient in a population of patients, and use each unique model to determine whether each patient is experiencing corrupt or inaccurate sensory perceptions.

In some embodiments, the statistical model may be implemented in the form of a neural network. In some embodiments, the statistical model may be implemented in the form of linear regression, non-linear regression, penalized regression techniques such as LASSO or Ridge regression, orthogonal matching pursuit, mutual information, Bayesian regression, stochastic gradient descent, a passive aggressive algorithm, linear or non-linear discriminant analysis, kernel regression, support vector machines, nearest neighbor algorithms, Gaussian processes, cross decomposition, naïve Bayes, decision tree algorithms and other ensemble methods including but not limited to Random Forest and gradient boosting, and neural network models including but not limited to perceptrons, convolutional neural networks, and deep neural networks.

The measure of correspondence may be any output of the statistical model, including but not limited to correlation, mutual information, or any discrete or continuous value returned by a function which takes as input signals from the neural module(s) and or the sensor module(s).

The correspondence may be determined in part via supervised learning algorithms which occurs either online within the device, or offline during the design and manufacture of the device. These supervised learning algorithms would use as training data labeled examples of typical and atypical neural data, labeled examples of sensory data in different kinds of environments, and labeled examples of agreements and disagreements between sensory and neural data. For example, sensory and neural data from actual hallucination episodes, as well as from normal activity, may be in included in the training set.

The correspondence may be determined using several different features of neural data, including raw signals, frequency-filtered signals, action potentials, local field potentials, or any other signal emitted by the nervous system. They may be processed and analyzed in the time domain or in the frequency domain. They may contain spatial information about the locations of the neural data probes.

The computation of correspondence may exploit known anatomical or functional connectivity patterns in the nervous system. For example, if it is known that brain area V1 is afferent to brain area V2, then the correspondence module may exploit the expectation that data recorded from V1 and V2 may have a certain causal relationship, such as a specific range of time or phase lags. Thusly, deviation from these expected values could be an indication of low correspondence.

The correspondence may be determined using several different features of environmental sensor data, including raw signals or frequency-filtered signals. They may be processed and analyzed in the time domain or in the frequency domain. They may contain spatial information about the locations of the sensors and imputed locations of matter or energy in the environment.

In some embodiments, the correspondence module may include an on-line decoder and an error detector that are configured to determine a degree of correspondence between the neural data and the real-world sensor data. In some cases, the correspondence may be based on a statistical model. In some cases, the correspondence may be based on information theory, such as the mutual information between the neural data and the real-world sensor data from one or more real-world sensors. In some cases, the correspondence may be determined by machine learning algorithms, including but not limited to those that determine whether a set of data are likely to belong to a particular class, for example the class of hallucination-related neural signals. The decoder may infer audio signals from the neural data and/or the sensor data. For example, the decoder may include one or more instances of speech recognition software. The speech recognition software may be used to reconstruct speech and other sounds from neural signals that are recorded by the one or more neural interface probes implanted in an area of the brain associated with auditory processing. The one or more sensors may comprise audio sensors. The speech recognition software may be used to reconstruct speech and other sounds recorded by the audio sensors. The correspondence module may then compare the reconstructed neural perception of sound to the real audio environment captured by the one or more audio sensors in order to detect whether the neural representations of speech and other sounds correspond to real-life audio stimuli, or whether they correspond to corrupt or inaccurate auditory perceptions.

In some cases, the decoder may infer visual signals from the neural data and/or the sensor data. For instance, the decoder may include one or more instances of image recognition software. The image recognition software may comprise facial recognition, object recognition, or scene segmentation software. The image recognition software may be used to reconstruct neural representations of visual data that are recorded by the one or more massively parallel neural interface probes implanted in an area of the brain associated with visual processing. The one or more sensors may comprise image sensors. The image recognition software may be used to reconstruct images and other visual data recorded by the image sensors. The reconstructed neural perception of visual data may then be compared with the real-world image data captured by one or more imaging devices, in order to detect whether the neural representations of visual data correspond to real-life visual stimuli, or whether they correspond to corrupt or inaccurate visual perceptions.

In some cases, the decoder may infer spatial locations from the neural data and/or the sensor data. For instance, the decoder may include one or more instances of spatial location software. The spatial location software may be used to reconstruct neural representations of spatial location data that are recorded by the one or more massively parallel neural interface probes implanted in an area of the brain associated with spatial location processing. The one or more sensor may comprise spatial location sensors. The spatial location software may be used to reconstruct the spatial location of the patient based on signals recorded from the spatial location sensors. The reconstructed neural perception of spatial location may then be compared with the real-world spatial location data captured by one or more spatial location sensors, in order to detect whether the neural representations of spatial location correspond to the real-life location, or whether they correspond to faulty cognitive processing.

In some cases, the decoder may compare neural data and sensor data that are different in nature. For instance, the decoder may reconstruct neural representations of speech or other sound that are recorded by the one or more massively parallel neural interface probes. The reconstructed neural perception of sound data may then be compared with the real-world image data captured by one or more imaging devices. If, for instance, the reconstructed neural perception indicates that the patient is hearing a voice, but the image data indicates that no one is in the room with the patient, this may be an indication that the patient is experiencing corrupt or inaccurate sensory representations. Similarly, the decoder may compare any form of neural data with any form of sensor data.

The error detector may be configured to generate an error signal that represents a lack of correspondence. The error signal may reflect only a lack of correspondence, or may reflect any other indication that the neural data is unusual and/or reflects a lack of physical or mental health.

The error signal may be indicative of the patient experiencing an episode of corrupt or inaccurate sensory perceptions. In some embodiments, the decision module may act on the error signal to actuate a visual signal and/or an audio signal to the patient to indicate that an error is detected. The visual signal may comprise a flashing light, and the audible signal may comprise an audible alarm. The visual and/or audio signals may be used to notify the patient that he/she is hallucinating, and to prompt the patient to revert back to reality. The signals may be produced externally to the patient or may signal the patient through neural stimulation. For instance, the signals may evoke the perception of a beep rather than producing a beep that would be audible to others.

The output from the decoder may be transmitted to allow remote monitoring. For instance, the output from the decoder may be transmitted to a patient's doctor or hospital for remote monitoring. The remote monitoring may allow the patient's doctor or hospital to note when the patient has experienced sensory data that does not align with reality. The remote monitoring may allow the patient's doctor or hospital to intervene. For instance, the remote monitoring may allow the patient's doctor or hospital to call the patient for a follow-up visit, or to send a reminder to the patient to take medication intended to lessen the hallucinatory effects of the patient's condition. The transmission of the output from the decoder may be via any wired communication means or wireless communication means. The wired communication may be via Ethernet. The wireless communication may be via Wi-Fi. The wireless communication may be via a cellular network. The wireless communication may be via a cellular networking protocol such as Global System for Mobile Communications (GSM), General Packet Radio Service (GPRS), Code Division Multiple Access (CDMA), CDMA 2000, Evolution Data Maximized (EV-DO), Frequency Division Multiple Access (FDMA), Time Division Multiple Access, 1st generation (1G), 2nd generation (2G), 3rd generation (3G), 4th generation (4G), 5th generation (5G), or any other cellular networking protocol. The wireless communication may be via an Institute of Electrical and Electronics Engineers (IEEE) wireless protocol, such as 802.11a, 802.11b, 802.11g, 802.11n, 802.11ac, 802.11ad, 802.11af, 802.11ah, 802.11ai, 802.11aj, 802.11aq, 802.11ax, 802.11ay, or any other IEEE wireless protocol. The wireless communication may be a via a Bluetooth wireless protocol. The wireless communication may be via any IEEE standard for wired or wireless communication.

The ability to detect when the brain is misprocessing or even creating sensory percepts would allow for better treatment of the conditions underlying these symptoms. For instance, detecting a hallucination associated with chronic schizophrenia could trigger an automatic dose of medication or would allow for remote monitoring of patients that do not elect for institutional care. As an example, a healthcare provider can use information, including the degree of correspondence, to assist the patient in managing the mental disorders through counseling, medication, electrical neural stimuli, etc.

Figure 2:
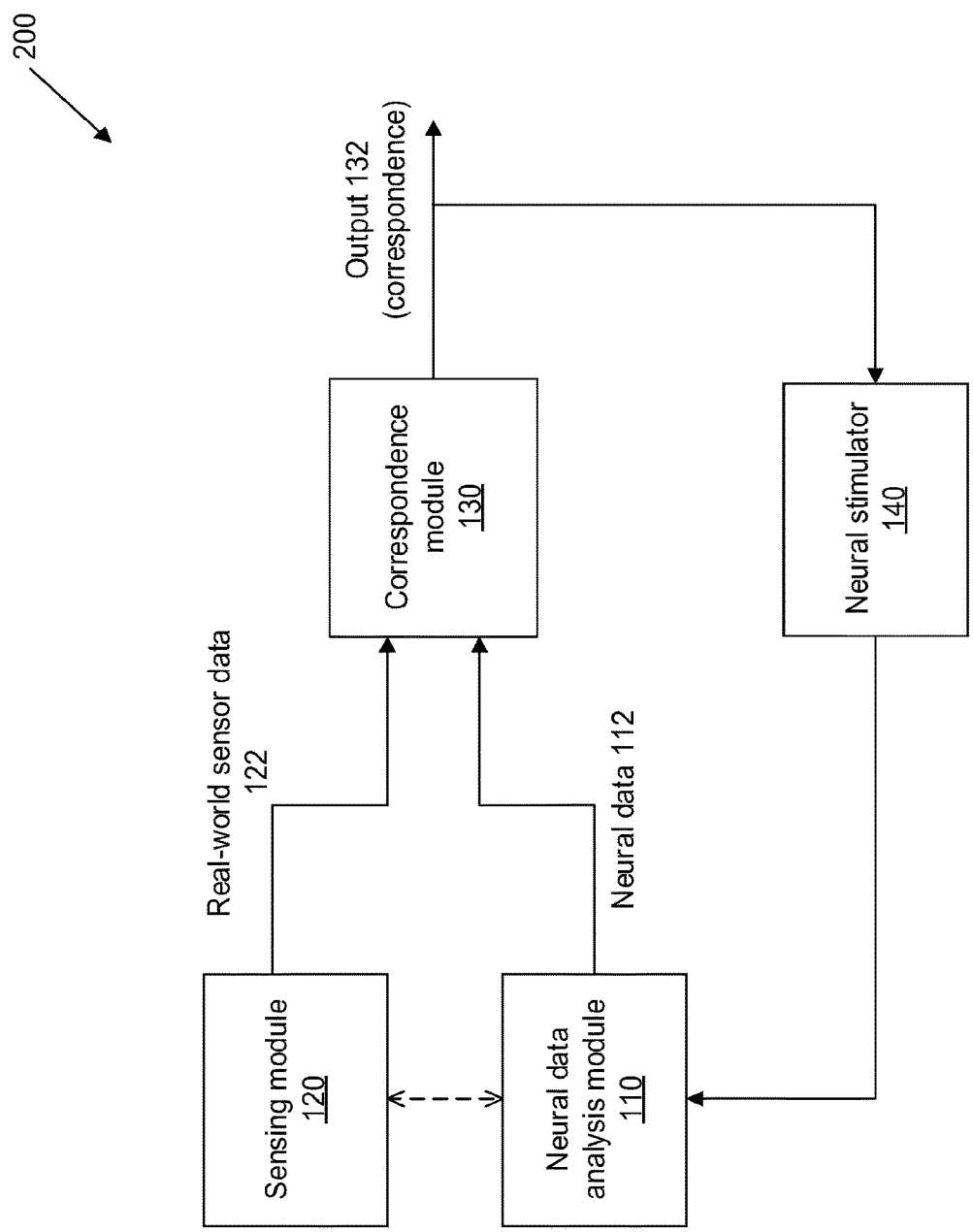
FIG. 2 illustrates a closed-loop neural data correspondence system comprising a neural stimulator, in accordance with some embodiments.

FIG. 2 illustrates a closed-loop system comprising a neural stimulator, in accordance with some embodiments. The system 200 may comprise the neural data analysis module 110 that outputs neural data 112, the sensing module 120 that outputs real-world sensor data 122, the correspondence module that outputs a degree of correspondence 132, and the decision module. The system may further comprise a neural stimulator 140.

The output 132 may be provided to the neural stimulator. In some cases, the neural stimulator may be a medical device (such as an implanted medical device) that is capable of automatically dispensing a predetermined dosage of medication based on the output 132 (i.e. whether the patient is or is not experiencing corrupt or inaccurate sensory perceptions). Alternatively, the neural stimulator may be configured to vary a dispensed dosage to the patient depending on the degree of correspondence (i.e. the extent and/or degree of corrupt or inaccurate sensory perceptions).

The output 132 may be a signal to communicate with another biological device. For example, it may be a signal to change the amplitude or frequency of a deep-brain stimulation device separately implanted in the patient.

In some embodiments, the neural stimulator may be implemented on one or more massively parallel neural interface probes. Such one or more massively parallel neural interface probes may include an electrode array that is capable of interrupting hallucinatory (pathological) precepts, in addition to being able to stimulate and record neural activity. The neural stimulator may be configured to impart a change in the mental status of the patient. Such a change may be detected by the neural data analysis module, which may give rise to altered neural data and an altered degree of correspondence. This may have the effect of altering the action taken by the neural stimulator. In this manner, the system 200 may comprise a feedback loop between the neural data and the action taken by the neural stimulator.

The output from the decoder may be used to trigger the release or administration of a pharmaceutical. The pharmaceutical may be a pharmaceutical prescribed by the patient's doctor to lessen the hallucinatory effects of the patient's condition. The decoder may be communicatively coupled with a device that administers the pharmaceutical. The coupling may be via any wired communication means or wireless communication means. The wireless communication may be via Bluetooth. The wireless communication may be via a cellular network. The device may administer the pharmaceutical intravenously. The device may administer the pharmaceutical intramuscularly. The device may administer the pharmaceutical transdermally. The device may administer the pharmaceutical orally. The device may administer the pharmaceutical intracranially, intraventricularly, or intraperitoneally.

The pharmaceutical may be a pharmaceutical intended to treat effects of psychosis disorders, such as schizophrenia. For instance, the pharmaceutical may be any of the following: chlorprothixene, levomepromazine, perazine, promethazine, prothipendyl, sulpiride, thioridazine, zuclopenthixol, perphenazine, benperidol, bromperidol, fluphenazine or its salts, fluspirilen, haloperidol, pimozide, amisulpride, aripiprazole, asenapine, chlorpromazine, clozapine, flupenthixol, iloperidone, melperone, olanzapine, paliperidone, penfluridol, quetiapine, risperidone, sertindole, thiothixene, trifluoperazine, ziprasidone, zotepine, or pericyazine. The pharmaceutical may be any other pharmaceutical intended to treat the effects of psychosis disorders.

The pharmaceutical may be intended to treat the effects of idiopathic pain. For instance, the pharmaceutical may be any of the following: a non-steroidal anti-inflammatory drug (such as paracetamol, acetaminophen, aspirin, naproxen, or ibuprofen), an opioid (such as codeine, morphine, or fentanyl), a muscle relaxant (such as diazepam), an anti-convulsant (such as gabapentin or pregabalin), an anti-depressant (such as amitriptyline), or a steroid. The pharmaceutical may be any pharmaceutical that alleviates idiopathic pain.

The pharmaceutical may be a pharmaceutical intended to treat effects of Alzheimer's disease or other forms of dementia. For instance, the pharmaceutical may be an acethylcholinesterase inhibitor, such as tacrine, rivastigmine, galantamine, or donepezil. The pharmaceutical may be a N-methyl-D-asparate (NMDA) receptor antagonist, such as memantine. The pharmaceutical may be any pharmaceutical intended to treat effects of Alzheimer's disease or other forms of dementia. The pharmaceutical may be any pharmaceutical intended to treat the effects on any other psychiatric disorder.

Figure 3:
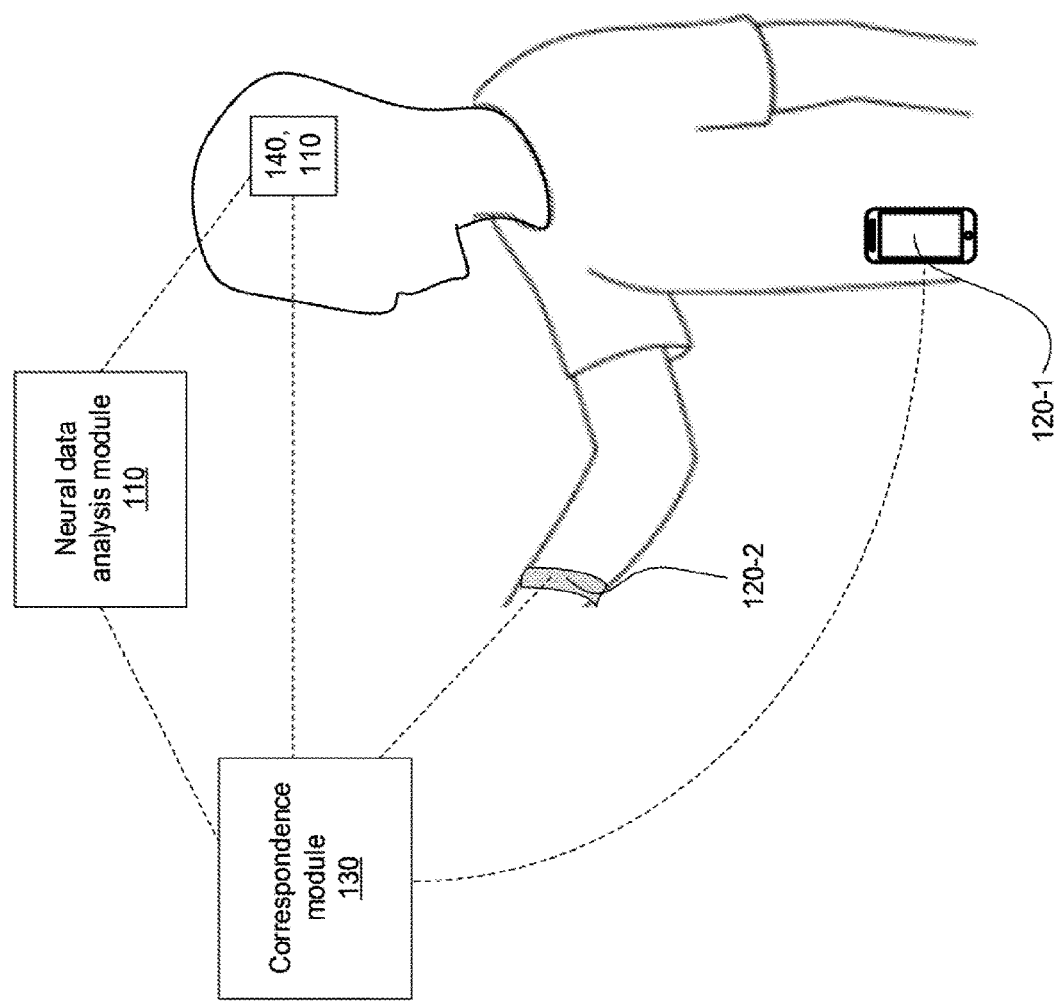
FIG. 3 illustrates the communication between different body-mounted sensors, an implanted neural interface probe, a neural data analysis module, and a correspondence module, in accordance with some embodiments.

FIG. 3 illustrates the communication between different body-mounted sensors, an implanted neural interface probe, a neural data analysis module, and a correspondence module, in accordance with some embodiments. The neural analysis module 110 may be implanted into the patient's brain in any of the manners described above. The neural data analysis may be communicatively coupled to sensing modules 120-1 and/or 120-2. The sensing module 120-1 may be a component of a mobile device carried by the patient, which may include one or more sensors such as cameras, microphones, accelerometers, gyroscopes, compasses, GPS, etc. The sensing module 120-2 may be a component of a wrist-wearable device such as a smartwatch or wristband, which may include on or more sensors for measuring body temperature, heart rate, location, motion of the wrist, etc.

The neural analysis module 110 and sensing modules 120-1 and/or 120-2 may be communicatively couple to the correspondence module 130. The correspondence module may be an app or other program held in memory on the mobile device and/or wrist-wearable device. The correspondence module may be peripheral hardware components communicatively coupled to the mobile device and/or wrist-wearable device. The neural stimulator 140 may also be implanted into the patient's brain in the manners described above.

Figure 4:
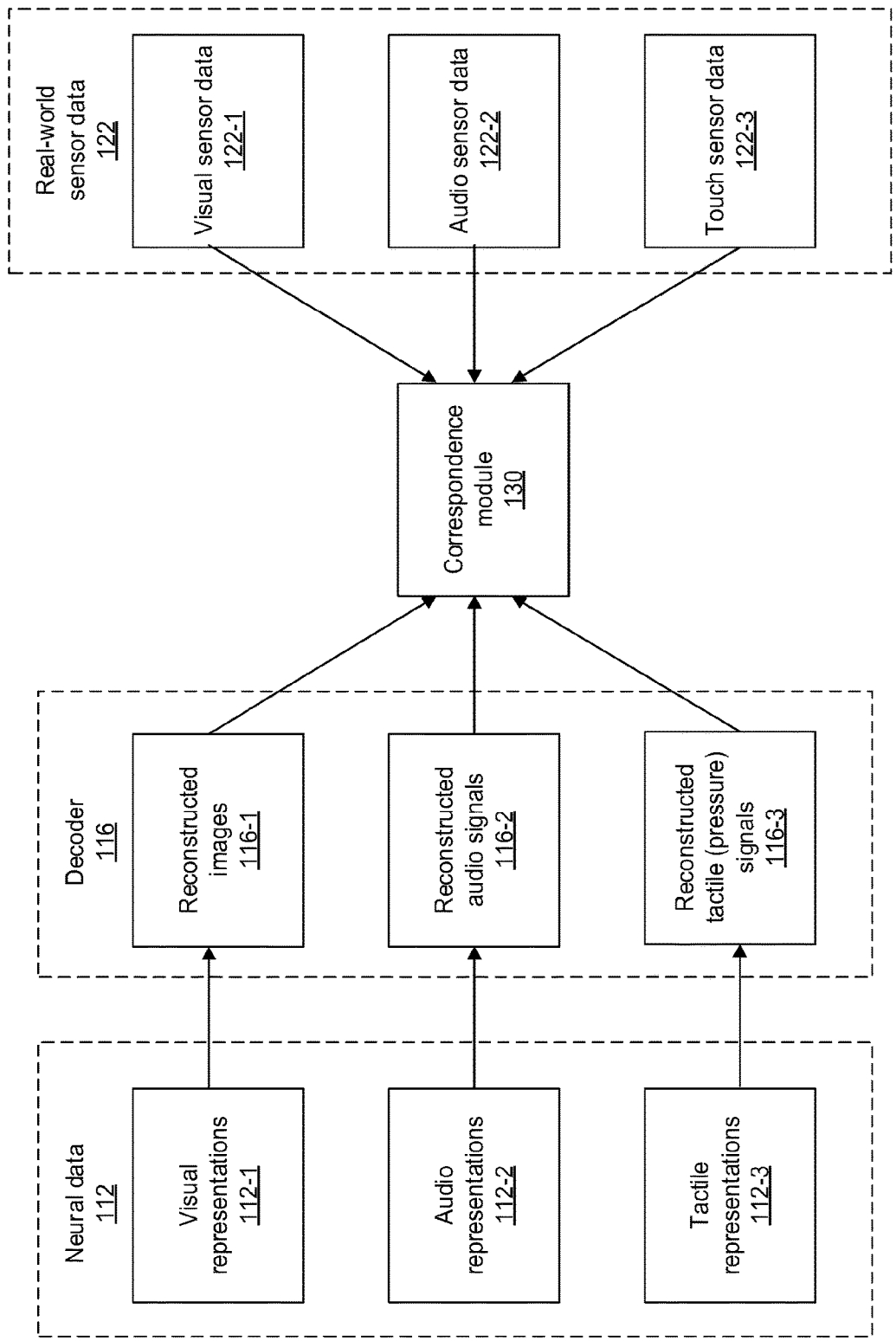
FIG. 4 illustrates the reconstruction of perceptions from neural data and correspondence of the perceptions with real-world sensor data, in accordance with some embodiments.

FIG. 4 illustrates the reconstruction of perceptions from neural data and correspondence of the perceptions with real-world sensor data, in accordance with some embodiments. The neural data 112 may be the output from one or more massively parallel neural interface probes, as described above. The neural data may comprise one or more of visual representations (e.g. those representations arising from areas of the brain associated with vision processing, such as the primary visual cortex or fusiform gyms) 112-1, audio representations (e.g. those representations arising from areas of the brain associated with auditory processing, such as the auditory cortex) 112-2, or tactile representations (e.g. those representations arising from areas of the brain associated with spatial or locational awareness, such as the "place" cells of the hippocampus or the "grid" cells of the entorhinal cortex) 112-3.

The neural data may be passed to the decoder 116. The decoder may process the neural data to form one or more reconstructed signals. For instance, the visual representations 112-1 may be processed to form reconstructed images 116-1. The audio representations 112-2 may be processed to form reconstructed audio signals 116-2. The tactile representations may be processed to form reconstructed tactile signals 116-3. Any of these representations may be processed alone or in combination with other representations.

The real-world sensor data 122 may be the output from one or more sensors, as described above. The sensor data may comprise one or more of visual sensor data (e.g. data from imaging devices capable of detecting visible, infrared, or ultraviolet, such as cameras) 122-1, audio sensor data (e.g. data from audio sensors such as microphones) 122-2, or touch sensor data (e.g. data from touch sensors such as capacitive touch sensors) 122-3. One or more of the reconstructed images, reconstructed audio signals, or reconstructed tactile signals may be sent to the correspondence module 130. Similarly, one or more of the visual sensor data, audio sensor data, or touch sensor data may be sent to the correspondence module. The correspondence module may act to determine a correspondence between the decoded neural data 116 and the real-world sensor data 122 using algorithms based in part on statistical analysis, information theory, machine learning, signal processing, pattern recognition, and/or detection theory. An algorithm may assume a certain statistical model and try to detect whether a patient is experiencing corrupt or inaccurate sensory perceptions based on the model. Alternatively, the algorithm may assume no model and simply compare the sensory and neural data using machine learning approaches.

Figure 5:
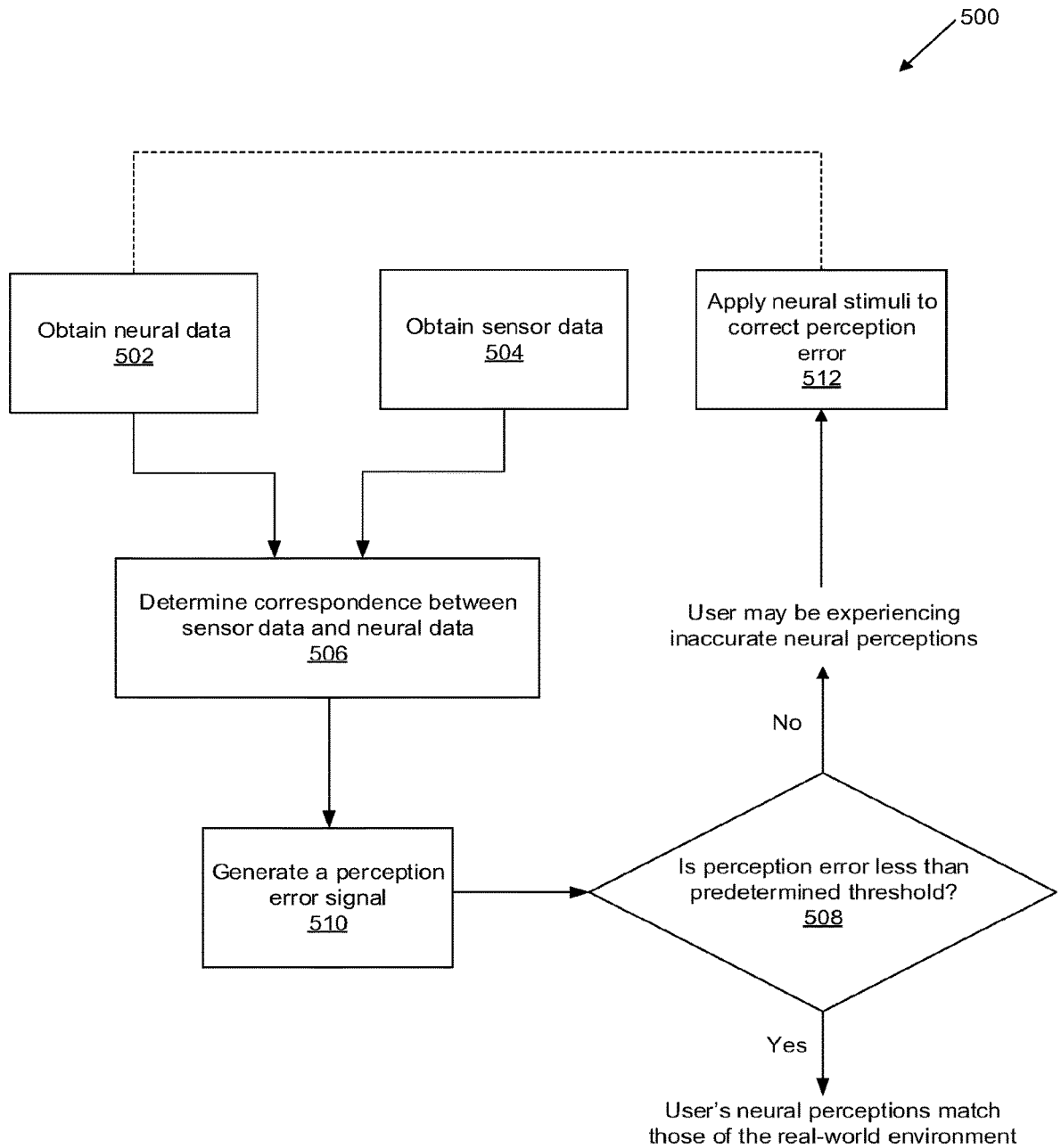
FIG. 5 is a flowchart of a method of monitoring and correcting neural perception errors, in accordance with some embodiments.

FIG. 5 shows an exemplary method 500 by which neural activity may be recorded and compared to data obtained from a sensor, allowing for the detection of corrupt or inaccurate sensory representations. The method 500 comprises obtaining neural data; obtaining sensor data; determining a correspondence between the sensor data and the neural data; determining whether a perception error is less than a predetermined threshold; and, if the perception error is too high: concluding that the user may be experiencing inaccurate neural perceptions; generating a perception error signal; and, optionally, applying neural stimuli to correct the perception error. In some embodiments, method 500 may be performed automatically by a processor associated with a computer readable memory.

In step 502, neural data is obtained by a neural data analysis module. The neural signals may be collected using a plurality of wires or microelectrodes that have been implanted into deep neural matter or superficial neural matter. The plurality of wires or microelectrodes may be part of one or more massively parallel neural interface probes that are configured to be implanted into one or more areas of a person's brain. The one or more neural interface probes can be configured to record information associated with neural activity and produce an output that represents neural activity. In some embodiments, the neural data analysis module may generate an analog or digital signal corresponding to neural activity patterns. The neural code may comprise representations of one or more neural activities associated with a plurality of neural events detected from the neural signals.

In some cases, the neural interface probes may comprise one or more neural detection channels. For instance, the neural interface probes may comprise more than 10, more than 100, more than 1000, more than 10000, more than 100000, or more than 1000000 neural detection channels. The neural detection channels may comprise electrodes, microwires, optical sensors, magnetic field sensors, or any other sensor. In some embodiments, the one or more neural interface probes may include a microwire bundle bonded to a CMOS array. In other embodiments, the one or more neural interface probes may include an array of silicon microelectrode probes that are bonded to a CMOS array, such that each electrode site is routed to a unique array position. In other embodiments, the neural interface may consist of scalp electrodes. In other embodiments, the neural interface may consist of electrodes placed on the surface of the brain or the surface of the dura mater. In other embodiments, the neural interface may record magnetic or optical signals from the nervous system.

The massively parallel neural interface probes can be implanted into different areas of the brain associated with different sensory processing (e.g., visual, auditory, tactile, taste, smell, position/movement, interoception, etc.). In one example, one or more neural interface probes may be implanted in an area of the brain associated with auditory processing, such as the auditory cortex. In another example, one or more neural interface probes may be implanted in an area of the brain associated with visual processing, such as the primary visual cortex or fusiform gyms.

In yet another example, one or more neural interface probes may be implanted in an area of the brain associated with spatial or locational awareness. For instance, the one or more neural interface probes may be implanted in the hippocampus and configured to record neural signals from "place" cells located in the hippocampus. Alternatively, the one or more neural interface probes may be implanted in the entorhinal cortex and configured to record neural signals from "grid" cells located in the entorhinal cortex.

In step 504, sensor data is obtained by a sensor module. The sensor data may be obtained from one or more types of sensors that are configured to detect real-world environmental stimuli. The real-world environmental stimuli are indicative of reality, as opposed to the corrupt or inaccurate sensory perceptions perceptions that a patient may be experiencing. The real-world environmental stimuli may be provided in the form of visual, auditory, tactile, taste, smell, position/movement, and/or interoception.

Examples of types of sensors may include inertial sensors (e.g. accelerometers, gyroscopes, and/or gravity detection sensors, which may form inertial measurement units (IMUs)), location sensors (e.g. global positioning system (GPS) sensors, mobile device transmitters enabling location triangulation), heart rate monitors, external temperature sensors, skin temperature sensors, capacitive touch sensors, sensors configured to detect a galvanic skin response (GSR), vision sensors (e.g. imaging devices capable of detecting visible, infrared, or ultraviolet light, such as cameras), proximity or range sensors (e.g. ultrasonic sensors, lidar, time-of-flight or depth cameras), altitude sensors, attitude sensors (e.g. compasses), pressure sensors (e.g. barometers), humidity sensors, vibration sensors, audio sensors (e.g. microphones), and/or field sensors (e.g. magnetometers, electromagnetic sensors, radio sensors).

The sensing module may further include one or more devices capable of emitting a signal into an environment. For instance, the sensing module may include an emitter along an electromagnetic spectrum (e.g. visible light emitter, ultraviolet emitter, infrared emitter). The sensing module may include a laser or any other type of electromagnetic emitter. The sensing module may emit one or more vibrations, such as ultrasonic signals. The sensing module may emit audible sounds (e.g. from a speaker). The sensing module may emit wireless signals, such as radio signals or other types of signals.

In some cases, one or more of the sensors may establish an absolute, relative, or contextual location. For instance, one or more of the sensors may be a global positioning system (GPS) sensor that determines the person's longitude and latitude. Such a GPS sensor may provide absolute location, such as that the person is located at 39.7392° N, 104.9903° W. The one or more sensors may be any sensor that determines an absolute location. As another example, one or more of the sensors may be a wireless detector that receives a signal from a specific location. Such a detector may provide relative location, such as that the person is located 300 meters north of their house. The one or more sensors may be any sensor that determines a relative location. As yet another example, one or more of the sensors may be a sensor that provides contextual information, such as that the person is at their place of work. The one or more sensors may be any sensor that determines a contextual location.

In some embodiments, one or more sensors of the sensing module may be incorporated into a wearable device. Examples of wearable devices may include smartwatches, wristbands, glasses, gloves, headgear (such as hats, helmets, virtual reality headsets, augmented reality headsets, head-mounted devices (HMD), headbands), pendants, armbands, leg bands, shoes, vests, motion sensing devices, etc. The wearable device may be configured to be worn on a part of a user's body (e.g. a smartwatch or wristband may be worn on the user's wrist).

Steps 502 and 504 may be performed substantially in real-time. Additionally, steps 502 and 504 may be performed in parallel.

In step 506, a correspondence is determined between the sensor data and the neural data by a correspondence module. The correspondence module can be used to detect corrupt or inaccurate sensory representations. The correspondence module may be configured to receive (a) neural data from the neural data analysis module and (b) real-world sensor data from the sensing module. The correspondence module may further analyze and compare the neural data and sensor data, so as to generate an output that is indicative of a degree of correspondence between perceptions obtained from the neural data with respect to the real-world environmental stimuli. The degree of correspondence may indicate whether a patient is experiencing corrupt or inaccurate sensory perceptions or is accurately experiencing reality. In some cases, the degree of correspondence may indicate an extent or severity of a patient's corrupt or inaccurate sensory perceptions.

The correspondence module may be implemented anywhere within the neural data correspondence system and/or outside of the neural data correspondence system. In some embodiments, the correspondence module may be implemented on a server. In other embodiments, the correspondence module may be implemented on a wearable device described elsewhere herein. In still other embodiments, the correspondence module may be implemented on a portable electronic device, such as a smartphone, tablet computer, or laptop computer. Additionally, the correspondence module may be implemented in the neural data analysis module. Alternatively, the correspondence module may be implemented in the sensor module. In other embodiments, the correspondence module may be implemented in both the neural data analysis module and the sensor module, or external to both the neural data analysis module and the sensor module. The correspondence module may be implemented using software, hardware, or a combination of software and hardware in one or more of the above-mentioned components within the neural data correspondence system.

The correspondence module may be capable of determining a correspondence between the neural data and the real-world sensor data using algorithms based in part on statistical analysis, information theory, machine learning, signal processing, pattern recognition, and/or detection theory. An algorithm may assume a certain statistical model and try to detect whether a patient is experiencing corrupt or inaccurate sensory perceptions based on the model. The statistical model may be based on Bayesian statistics. The algorithm may also estimate a different statistical model for each patient in a population of patients, and use each unique model to determine whether each patient is experiencing corrupt or inaccurate sensory perceptions. In some embodiments, the statistical model may be implemented in the form of a Bayesian model. In some embodiments, the implementation may be via machine learning algorithms.

In some embodiments, the correspondence module may include algorithms to determine a degree of correspondence between the neural data and the real-world sensor data based on a statistical model, information theory, or other machine learning approach. The algorithms may take as inputs features selected from the neural data and/or the sensor data, such as audio-related signals. For example, the decoder may include one or more instances of speech recognition software. The speech recognition software may be used to reconstruct neural representations of speech and other sounds that are recorded by the one or more massively parallel neural interface probes implanted in an area of the brain associated with auditory processing. The one or more sensors may comprise audio sensors. The speech recognition software may be used to reconstruct speech and other sounds recorded by the audio sensors. The correspondence module may then compare the reconstructed neural perception of sound to the real audio environment captured by the one or more audio sensors in order to detect whether the neural representations of speech and other sounds correspond to real-life audio stimuli, or whether they correspond to corrupt or inaccurate auditory perceptions.

In some cases, the correspondence module may accomplish the same goal as in the previous paragraph, but for visual signals, and via image recognition software. The image recognition software may comprise facial recognition, object recognition, or scene segmentation software. The image recognition software may be used to reconstruct neural representations of visual data that are recorded by the one or more massively parallel neural interface probes implanted in an area of the brain associated with visual processing. The one or more sensors may comprise image sensors. The image recognition software may be used to reconstruct images and other visual data recorded by the image sensors. The reconstructed neural perception of visual data may then be compared with the real world image data captured by one or more imaging devices, in order to detect whether the neural representations of visual data correspond to real-life visual stimuli, or whether they correspond to corrupt or inaccurate visual perceptions.

In some cases, the decoder may accomplish the same goal as in the previous paragraph, but for spatial locations and via spatial location software. The spatial location software may be used to reconstruct neural representations of spatial location data that are recorded by the one or more massively parallel neural interface probes implanted in an area of the brain associated with spatial location processing. The one or more sensor may comprise spatial location sensors. The spatial location software may be used to reconstruct the spatial location of the patient based on signals recorded from the spatial location sensors. The reconstructed neural perception of spatial location may then be compared with the real-world spatial location data captured by one or more spatial location sensors, in order to detect whether the neural representations of spatial location correspond to the real-life location, or whether they correspond to faulty cognitive processing.

In some cases, the correspondence module may compare neural data and sensor data from different modalities. For instance, the decoder may reconstruct neural representations of speech or other sound that are recorded by the one or more massively parallel neural interface probes. The reconstructed neural perception of sound data may then be compared with the real-world image data captured by one or more imaging devices. If, for instance, the reconstructed neural perception indicates that the patient is hearing a voice, but the image data indicates that no one is in the room with the patient, this may be an indication that the patient is experiencing corrupt or inaccurate sensory representations. Similarly, the decoder may compare any form of neural data with any form of sensor data.

In step 508, it is determined whether the error signal arising in part from the correspondence module is sufficient to execute an action. The error signal may be related to the degree of agreement between the neural data and the sensor data. Alternatively it may be related to some property of the neural data alone. If the error signal is low, this may be taken to be indicative that the user's neural perceptions match those of the real-world environment. If the perception error is large, this may be taken to be indicative that the user may be experiencing inaccurate neural perceptions. Error signals of sufficient magnitude—which may depend on context such as patient identity, patient history, patient biomarkers, clinician preferences, or other covariates—will trigger an action signal from the decision module. In some embodiments, a receiver operating characteristic (ROC) curve can be created based on a magnitude of the error signal to provide a sensitivity/specificity report. The ROC curve is a tool for diagnostic test evaluation, in which the true positive rate (sensitivity) is plotted in function of the false positive rate (specificity) for different cut-off points of a parameter. Each point on the ROC curve represents a sensitivity/specificity pair corresponding to a particular decision threshold. The area under the ROC curve (AUC) is a measure of how well a parameter can distinguish between two diagnostic groups (hallucination versus normal perceptions).

In step 510, the decision module generates an action signal if the error signal is too high in step 508. The error signal may be too high when the neural data and the real-world sensor data fail to meet a predetermined correspondence threshold. Alternatively, the error signal may be high due to properties of the neural data alone. The error signal may be indicative of the patient experiencing an episode of corrupt or inaccurate sensory perceptions. In some embodiments, the action signal may be an output that triggers another device to execute a corresponding action. For instance, the action signal may trigger a visual signal and/or an audio signal to the patient to indicate that an error is detected. The visual signal may comprise a flashing light, and the audible signal may comprise an audible alarm. The visual and/or audio signals may be used to notify the patient that he/she is experiencing corrupt or inaccurate sensory perceptions, and to prompt the patient to revert back to reality. The signals may be produced externally to the patient or may signal the patient through neural stimulation. For instance, the signals may evoke the perception of a beep rather than producing a beep that would be audible to others.

The action signal may be transmitted to allow remote monitoring. For instance, the output from the decision module may be transmitted to a patient's doctor or hospital for remote monitoring. The remote monitoring may allow the patient's doctor or hospital to note when the patient has experienced sensory data that does not align with reality. The remote monitoring may allow the patient's doctor or hospital to intervene. For instance, the remote monitoring may allow the patient's doctor or hospital to call the patient for a follow-up visit, or to send a reminder to the patient to take medication intended to lessen the hallucinatory effects of the patient's condition. The transmission of the output from the decoder may be via any wired communication means or wireless communication means. The wired communication may be via Ethernet. The wireless communication may be via Wi-Fi. The wireless communication may be via a cellular network.

In step 512, neural stimuli may be applied to correct the perception error. The ability to detect when the brain is misprocessing or even creating sensory percepts would allow for better treatment of the conditions underlying these symptoms. For instance, detecting a hallucination associated with chronic schizophrenia could trigger an automatic dose of medication or would allow for remote monitoring of patients that do not elect for institutional care. As an example, a healthcare provider can use information, including any intermediate or final measure in the system, including any computed measure of correspondence, any aspect of the error signal, or the decision signal, to assist the patient in managing the mental disorders through counseling, medication, electrical neural stimuli, etc.

The neural stimuli may be applied by neural data correspondence system comprising a neural stimulator, in accordance with some embodiments. The system may comprise the neural data analysis module that outputs neural data, the sensing module that outputs real-world sensor data, and the correspondence module that outputs the correspondence.

The system may further comprise a neural stimulator. The output may be provided to the neural stimulator. In some cases, the neural stimulator may be an implanted medical device that is capable of automatically dispensing a predetermined dosage of medication based on the output (i.e. whether the patient is or is not experiencing corrupt or inaccurate sensory perceptions). Alternatively, the neural stimulator may be configured to vary a dispensed dosage to the patient depending on the correspondence (i.e. the extent and/or degree of corrupt or inaccurate sensory perceptions).

In some embodiments, the neural stimulator may be implemented on one or more massively parallel neural interface probes. Such one or more massively parallel neural interface probes may include an electrode array that is capable of interrupting hallucinatory (pathological) precepts, in addition to being able to stimulate and record neural activity. The neural stimulator may be configured to impart a change in the mental status of the patient. Such a change may be detected by the neural data analysis module, which may give rise to altered neural data and an altered degree of correspondence. This may have the effect of altering the action taken by the neural stimulator. In this manner, the system may comprise a feedback loop between the neural data, the sensory data, the correspondence module, and the decision module, and the action taken by the neural stimulator.

The output from the decoder may be used to trigger the release or administration of a pharmaceutical. The pharmaceutical may be a pharmaceutical prescribed by the patient's doctor to lessen the hallucinatory effects of the patient's condition. The decoder may be communicatively coupled with a device that administers the pharmaceutical. The coupling may be via any wired communication means or wireless communication means. The wireless communication may be via Bluetooth. The wireless communication may be via a cellular network. The device may administer the pharmaceutical intravenously. The device may administer the pharmaceutical intramuscularly. The device may administer the pharmaceutical transdermally. The device may administer the pharmaceutical orally.

The pharmaceutical may be a pharmaceutical intended to treat effects of psychosis disorders, such as schizophrenia. For instance, the pharmaceutical may be any of the following: chlorprothixene, levomepromazine, perazine, promethazine, prothipendyl, sulpiride, thioridazine, zuclopenthixol, perphenazine, benperidol, bromperidol, fluphenazine or its salts, fluspirilen, haloperidol, pimozide, amisulpride, aripiprazole, asenapine, chlorpromazine, clozapine, flupenthixol, iloperidone, melperone, olanzapine, paliperidone, penfluridol, quetiapine, risperidone, sertindole, thiothixene, trifluoperazine, ziprasidone, zotepine, or pericyazine. The pharmaceutical may be any other pharmaceutical intended to treat the effects of psychosis disorders.

The pharmaceutical may be intended to treat the effects of idiopathic pain. For instance, the pharmaceutical may be any of the following: a non-steroidal anti-inflammatory drug (such as paracetamol, acetaminophen, aspirin, naproxen, or ibuprofen), an opioid (such as codeine, morphine, or fentanyl), a muscle relaxant (such as diazepam), an anti-convulsant (such as gabapentin or pregabalin), an anti-depressant (such as amitriptyline), or a steroid. The pharmaceutical may be any pharmaceutical that alleviates idiopathic pain.

The pharmaceutical may be a pharmaceutical intended to treat effects of Alzheimer's disease or other forms of dementia. For instance, the pharmaceutical may be an acethylcholinesterase inhibitor, such as tacrine, rivastigmine, galantamine, or donepezil. The pharmaceutical may be a N-methyl-D-asparate (NMDA) receptor antagonist, such as memantine. The pharmaceutical may be any pharmaceutical intended to treat effects of Alzheimer's disease or other forms of dementia. The pharmaceutical may be any pharmaceutical intended to treat the effects on any other psychiatric disorder.

A person of ordinary skill in the art will recognize many variations, alterations and adaptations based on the disclosure provided herein. For example, the order of the steps of the method can be changed, some of the steps removed, some of the steps duplicated, and additional steps added as appropriate. Some of the steps may comprise sub-steps. Some of the steps may be automated and some of the steps may be manual. The processor as described herein may comprise one or more instructions to perform at least a portion of one or more steps of the method 500.

The method 500 may operate in a manner that does not require complete understanding of the mechanisms by which neural processes represent sensory data. Current research is just beginning to probe how neural signals give rise to simple behaviors. It will take many years of research activity to arrive at an understanding of neural processes that allows perfect interpretation of brain activity, if such an understanding is even possible. It may also not be necessary that the method provide complete, accurate decoding of neural representations.

Figure 6:
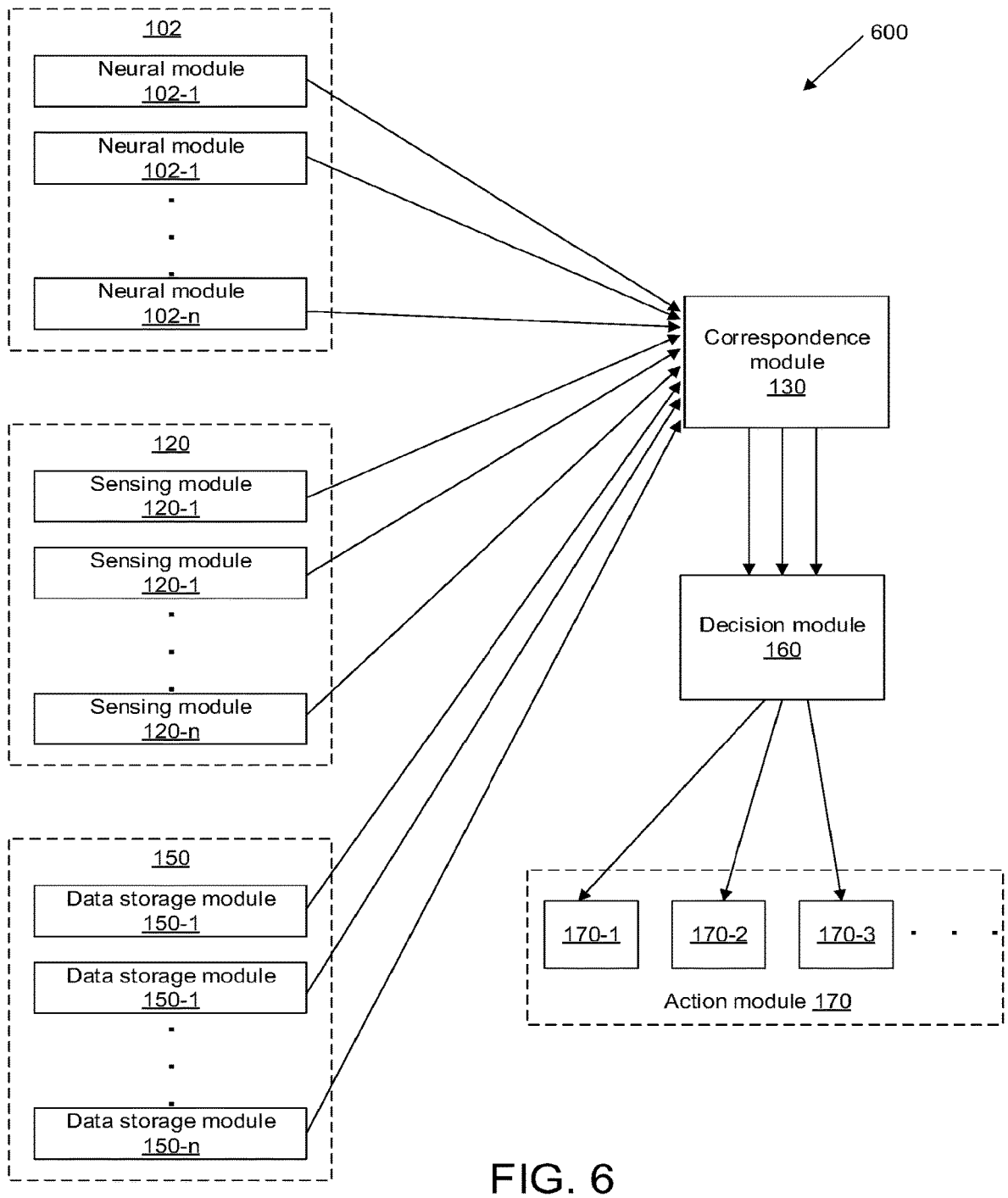
FIG. 6 illustrates a system for monitoring neural activity of a living subject, in accordance with some embodiments.

FIG. 6 illustrates a system for monitoring neural activity of a living subject, in accordance with some further embodiments. The living subject may be a human being (e.g. a patient). In one aspect, system 600 may comprise one or more neural modules 102 (e.g. 102-1 through 102-*n*), one or more sensing modules 120 (e.g. 120-1 through 120-*n*), one or more data storage modules 150 (e.g. 150-1 through 150-*n*), a correspondence module 130, a decision module 160, and one or more action modules 170 (e.g. 170-1 through 170-*n*). Each of the above may be operatively connected to one another via a network or any type of communication link that allows the transmission of data from one module or component to another.

The neural modules 102 may comprise any of the neural data analysis modules or devices described elsewhere herein. The neural modules may comprise the same type or different types of devices. The neural modules may include one or more devices configured to collect a plurality of signals from the nervous system of a living subject. The neural modules may include electroencephalography (EEG), electrocorticography (ECoG), intracranial electroencephalography (iEEG), microelectrode arrays, nerve cuffs, functional near infrared imaging, functional magnetic resonance imaging (fMRI), calcium imaging using genetically encoded calcium indicators or voltage sensitive proteins, and any other types of apparatus or technology that can be used to collect data from the nervous system of the living subject. One or more of the neural modules may be used in conjunction with the neural data analysis module described elsewhere herein.

The sensing modules 120 may include any of the sensing modules or sensors described elsewhere herein. In some embodiments, the sensing modules or sensors may include image sensors, microphones, inertial sensors such as accelerometers or gyroscopes, GPS, force sensors, capacitive touch sensors, temperature or thermal sensors, chemical sensors, and so forth.

The data storage modules 150 may include one or more memory devices configured to store data. Additionally or optionally, the data storage modules 150 may, in some embodiments, be implemented as a computer system with a storage device. The data storage modules 150 can be configured to store statistical prior data for one or more of the neural modules 102. The data storage modules 150 can also be configured to store statistical prior data for one or more of the neural modules 102 and their correspondences to the sensor data collected by the sensing modules 120.

The correspondence module 130 may include one or more embodiments of the correspondence module as described elsewhere herein. The decision module 160 may include one or more embodiments of the decision module as described elsewhere herein.

The action modules 170 may be configured to receive input from the decision module 160. Examples of action modules may include computing devices 170-1, therapeutic delivery devices 170-2, notification devices 170-3, and so forth. The computing devices and/or notification devices can be configured to provide alerts to the living subject (e.g., patient), and/or to other parties such as healthcare providers or emergency personnel. The notification devices can generate a visual signal and/or an audio signal to the patient to indicate presence, absence, or extent of a potential cognitive or physiological disturbance of the patient. The visual signal may comprise a flashing light, and the audible signal may comprise an audible alarm. For example, the visual and/or audio signals may be used to notify the patient that he/she is hallucinating, and to prompt the patient to revert back to reality. The signals may be produced externally to the patient or may signal the patient through neural stimulation. For instance, the signals may evoke the perception of a beep rather than producing a beep that would be audible to others. The therapeutic delivery devices can be used to deliver electrical simulation to the patient and/or provide pharmaceutical intervention (e.g. applying a medication dosage as described elsewhere herein).

In some embodiments, the correspondence module 130 may be configured to be in communication with (1) a neural module 102 and (2) one or more additional modules comprising a sensing module 120, another neural module 102, and/or a data storage module 150. The neural module(s) may be configured to collect neural data indicative of perceptions experienced by the living subject. The sensing module may be configured to collect (1) sensor data indicative of real-world information about an environment around the living subject, and/or (2) sensor data indicative of a physical state or physiological state of the living subject. The data storage module can be configured to store prior neural data and/or prior sensor data. The correspondence module can be configured to measure a correspondence (a) between the neural data collected by the neural module(s) and the sensor data collected by the sensing module, (b) between the neural data collected by two or more neural modules, and/or (c) between the neural data collected by the neural module(s) and the prior data stored in data storage module. The measured correspondence can be used, for example by the decision module 160, to determine a presence, absence, or extent of a potential cognitive or physiological disturbance of the living subject.

In some embodiments, the measured correspondence may comprise a level of agreement or disagreement (a) between the neural data collected by the neural module(s) and the sensor data collected by the sensing module, (b) between the neural data collected by two or more neural modules, and/or (c) between the neural data collected by the neural module (s) and the prior data stored in data storage module. The level of agreement or disagreement need not be binary, and can be measured along a continuum. In some cases, the level of agreement or disagreement may comprise multiple discrete levels. In some embodiments, the level of agreement or disagreement may be provided in the form of a multivariate vector. The correspondence module can be measure the correspondence using statistical models, information theory, or machine learning algorithms.

In some embodiments, the correspondence module can be configured to measure the correspondence (b) between the neural data collected by the two or more neural modules, without requiring or utilizing some or all of the sensor data collected by the sensing module. Additionally or optionally, the correspondence module can be configured measure the correspondence (c) between the neural data collected by the neural module(s) and the prior data stored in data storage module, without requiring or utilizing some or all of the sensor data collected by the sensing module.

The decision module 160 can be configured to determine the presence, absence, or extent of the potential cognitive or physiological disturbance based on the measured correspondence output by the correspondence module 130. The decision module can be further configured to generate one or more alerts, notifications, control signals, etc. to the action modules 170. For example, alerts or notifications can be sent to the patient or other parties such as healthcare providers, such alerts or notifications being indicative of the presence, absence, or extent of the potential cognitive or physiological disturbance. In some cases, the control signals can be sent to the therapeutic delivery devices, for example to deliver electrical simulation to the patient and/or provide pharmaceutical intervention (e.g. applying a medication dosage) to mitigate or counter the potential cognitive or physiological disturbance.

The systems and methods described herein may operate in a manner that does not require complete understanding of the mechanisms by which neural processes represent sensory data. Current research is just beginning to probe how neural signals give rise to simple behaviors. It will take many years of research activity to arrive at an understanding of neural processes that allows perfect interpretation of brain activity, if such an understanding is even possible. It may also not be necessary that the method provide complete, accurate decoding of neural representations. For instance, the systems and methods described herein may not require an understanding of neural activity at all, or of the sensory environment at all. The systems and methods may only require that neural signals and sensor signals be measureable and representable in an analog or digital form.

All that is required for the systems and methods to detect hallucinations or other corrupt or inaccurate sensory representations is that the output from the one or more massively parallel neural interface probes be correlated with the data from the one or more sensors. This creates a model (a prior hypothesis) against which all subsequent data from both the neural recording system and external sensors can be checked. This model may be updated based on advances in the understanding of neural processes or advances in methods and systems for processing neural signals. Regardless of the model, whenever the neural data and sensor data suddenly diverge, it may be concluded that there is a high probability (according to the model) that a hallucination or other pathological state has occurred.

For instance, the systems and method need not be able to accurately reconstruct the details of human faces from neural representations of visual data. It may be sufficient to simply determine that a patient is seeing some face from the neural representation of visual data. If the neural representation and the sensor data disagree about the presence of a face in the room, this may be taken as an indication that the patient is suffering a visual hallucination.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for monitoring neural activity of a living subject, comprising:
   a correspondence module configured to be in communication with (1) a neural interface module and (2) a plurality of additional modules comprising a sensing module, another neural interface module, or a data storage module,
   wherein the neural interface module(s) are configured to collect neural data from the living subject,
   wherein the sensing module is configured to collect (1) sensor data indicative of real-world information about an environment around the living subject, and/or (2) sensor data indicative of a physical state or physiological state of the living subject,
   wherein the data storage module is configured to store prior neural data and/or prior sensor data,
   wherein the correspondence module is configured to measure a correspondence (a) between the neural data collected by the neural interface module(s) and the sensor data collected by the sensing module or (b) between the neural data collected by two or more neural interface modules,
   the measured correspondence being indicative of a presence, absence, or extent of potential cognitive or physiological response or changes in the living subject,
   wherein the correspondence module comprises a decoder configured to reconstruct, from the neural data, (i) neural correlates of speech and sounds, or (ii) representations of speech and sounds.

2. The system of claim 1, wherein the measured correspondence comprises a level of agreement or disagreement (a) between the neural data collected by the neural interface module(s) and the sensor data collected by the sensing module or (b) between the neural data collected by two or more neural interface modules.

3. The system of claim 2, wherein the level of agreement or disagreement is measured along a continuum.

4. The system of claim 2, wherein the level of agreement or disagreement comprises a multivariate vector.

5. The system of claim 1, wherein the correspondence module is configured to measure the correspondence (b) between the neural data collected by the two or more neural interface modules, without requiring or utilizing some or all of the sensor data collected by the sensing module.

6. The system of claim 1, wherein the correspondence module is configured to further measure correspondence (c) between the neural data collected by the neural interface module(s) and the prior data stored in the data storage module, without requiring or utilizing some or all of the sensor data collected by the sensing module.

7. The system of claim 1, wherein the decoder comprises a speech recognition software configured to reconstruct from the neural data, (i) the neural correlates of speech and sounds or (ii) the representations of speech and sounds collected from one or areas of the subject's brain associated with acoustics.

8. The system of claim 7, wherein the correspondence module is configured to compare the neural correlates of speech and sounds or the representations of speech and sounds to audio data recorded by the sensing module in the living subject's vicinity, so as to determine (1) whether the neural correlates of speech and sounds or the representations of speech and sounds correspond to real-life audio stimuli, or (2) whether the neural correlates of speech and sounds or the representations of speech and sounds correspond to auditory hallucinations.

9. The system of claim 1, wherein the decoder further comprises an image recognition software configured to reconstruct, from the neural data, (i) neural correlates of visual data, or (ii) representations of visual data.

10. The system of claim 9, wherein the correspondence module is configured to compare the neural correlates of visual data or the representations of visual data to actual image data recorded by the sensing module in the living subject's vicinity, so as to determine (1) whether the neural correlates of visual data or the representations of visual data correspond to real-life visual stimuli, or (2) whether the neural correlates of visual data or the representations of visual data correspond to visual hallucinations.

11. The system of claim 1, wherein the correspondence module is configured to generate an error signal based on the degree of correspondence between the neural data and the sensor data and/or based on different sets of the neural data.

12. The system of claim 11, wherein the error signal is used to validate and improve an accuracy of the correspondence module.

13. The system of claim 11, wherein a high error signal results from low correspondence and is indicative that the living subject is experiencing inaccurate neural perceptions.

14. The system of claim 13, wherein the high error signal indicates that patterns of neural activity are atypical and/or unhealthy patterns of neural activity, or is indicative of the living subject experiencing a hallucination episode.

15. The system of claim 11, wherein a low error signal results from high correspondence and indicates that the living subject is experiencing neural perceptions matching real-world environmental stimuli.

16. The system of claim 15, wherein the low error signal indicates that patterns of neural activity are typical and/or healthy patterns of neural activity.

17. The system of claim 1, further comprising a decision module configured to determine the presence, absence, or extent of the potential cognitive or physiological response or changes based on the measured correspondence.

18. The system of claim 17, wherein the decision module is further configured to generate one or more alerts to the living subject and/or a healthcare provider, wherein said alerts are indicative of the presence, absence, or extent of the potential cognitive or physiological response or changes.

19. The system of claim 17, wherein the decision module is further configured to generate one or more control signals to one or more therapeutic delivery devices, to deliver device-based neuromodulation and/or pharmaceutical intervention to mitigate the potential cognitive or physiological response or changes.

20. The system of claim 1, wherein the correspondence module is configured to measure the correspondence (a)

between the neural data collected by the neural interface module(s) and the sensor data collected by the sensing module.

21. The system of claim 1, wherein the correspondence module is configured to measure the correspondence (b) between the neural data collected by the neural interface modules.

22. A system for monitoring neural activity of a living subject, comprising:
 a correspondence module configured to be in communication with (1) a neural interface module and (2) a plurality of additional modules comprising a sensing module, another neural interface module, or a data storage module,
 wherein the neural interface module(s) are configured to collect neural data from the living subject,
 wherein the sensing module is configured to collect (1) sensor data indicative of real-world information about an environment around the living subject, and/or (2) sensor data indicative of a physical state or physiological state of the living subject,
 wherein the data storage module is configured to store prior neural data and/or prior sensor data,
 wherein the correspondence module is configured to measure a correspondence (a) between the neural data collected by the neural interface module(s) and the sensor data collected by the sensing module or (b) between the neural data collected by two or more neural interface modules,
 the measured correspondence being indicative of a presence, absence, or extent of potential cognitive or physiological response or changes in the living subject,
 wherein the correspondence module comprises a decoder comprising an image recognition software configured to reconstruct, from the neural data, (i) neural correlates of visual data, or (ii) representations of visual data.

23. The system of claim 22, wherein the correspondence module is configured to compare the neural correlates of visual data or the representations of visual data to actual image data recorded by the sensing module in the living subject's vicinity, so as to determine (1) whether the neural correlates of visual data or the representations of visual data correspond to sensor data indicative of real-world information, or (2) whether the neural correlates of visual data or the representations of visual data correspond to visual hallucinations.

* * * * *